United States Patent [19]
Mikasa et al.

[11] Patent Number: 5,255,072
[45] Date of Patent: Oct. 19, 1993

[54] APPARATUS FOR ANALYZING FLUID BY MULTI-FLUID MODULATION MODE

[75] Inventors: Hajime Mikasa, Moriyama; Ichiro Asano, Kouka; Nobutaka Kihara, Nara; Shuichi Ishimoto, Kyoto; Isao Fujita, Simotubayashi; Norio Kada, Ibaraki; Takeshi Aoki, Kyoto; Takao Imaki, Nagaokakyo; Masahiko Fujiwara, Suita; Naohito Shimizu; Junji Kato, both of Kyoto, all of Japan

[73] Assignee: Horiba, Ltd., Kyoto, Japan

[21] Appl. No.: 820,146

[22] Filed: Jan. 13, 1992

Related U.S. Application Data

[62] Division of Ser. No. 278,046, Nov. 30, 1988.

[30] Foreign Application Priority Data

| Date | | Country | Number |
|---|---|---|---|
| Dec. 11, 1987 | [JP] | Japan | 62-314806 |
| Dec. 12, 1987 | [JP] | Japan | 62-315047 |
| Dec. 24, 1987 | [JP] | Japan | 62-328734 |
| Dec. 26, 1987 | [JP] | Japan | 62-335864 |
| Dec. 28, 1987 | [JP] | Japan | 62-335120 |
| Dec. 29, 1987 | [JP] | Japan | 62-335786 |
| Dec. 29, 1987 | [JP] | Japan | 62-335787 |
| Dec. 29, 1987 | [JP] | Japan | 62-335788 |
| Dec. 29, 1987 | [JP] | Japan | 62-335789 |
| Dec. 29, 1987 | [JP] | Japan | 62-335790 |
| Dec. 29, 1987 | [JP] | Japan | 62-335791 |
| Dec. 29, 1987 | [JP] | Japan | 62-335792 |
| Dec. 30, 1987 | [JP] | Japan | 62-201169 |
| Dec. 30, 1987 | [JP] | Japan | 62-336616 |

[51] Int. Cl.⁵ ............................................ G01N 21/85
[52] U.S. Cl. .................................... 356/432; 356/435; 356/436; 356/343; 356/434; 356/437; 250/343; 73/23.2; 422/83; 422/93; 436/52
[58] Field of Search ............... 356/432, 435, 436, 434, 356/437; 250/343, 345, 338.5; 73/23.2, 23.24; 422/93, 83; 436/147, 39, 52

[56] References Cited

U.S. PATENT DOCUMENTS

| | | | |
|---|---|---|---|
| 2,908,820 | 10/1959 | Parsons | 23/232 |
| 3,535,084 | 10/1970 | Izawa et al. | 23/232 |
| 3,915,645 | 10/1975 | Funke et al. | 23/232 |
| 3,967,933 | 7/1976 | Etess et al. | 23/232 |
| 4,256,964 | 3/1981 | Ishida et al. | 250/345 |
| 4,393,304 | 7/1983 | Ishida et al. | 250/343 |
| 4,550,084 | 10/1985 | Nelson et al. | 436/45 |
| 4,705,669 | 11/1987 | Tsuji et al. | 422/93 |
| 4,879,245 | 11/1989 | Ruse | 436/124 |

Primary Examiner—Vincent P. McGraw
Assistant Examiner—LaCharles P. Keesee
Attorney, Agent, or Firm—Price, Gess & Ubell

[57] ABSTRACT

A method and apparatus for analyzing fluid by a multi-fluid modulation mode is characterized by subjecting a plurality of sample fluids (which may be different or a single sample fluid divided into a plurality of systems) to a fluid modulation by reference fluids at various frequencies, respectively. An analytical portion provided with only one sensor is simultaneously and continuously supplied with the respective sample fluids. An output signal from the sensor in the analytical portion is divided into signal components of the respective modulation frequencies for the respective sample fluids to rectify and level, whereby obtaining analyzed values about the respective sample fluids is achieved.

10 Claims, 30 Drawing Sheets

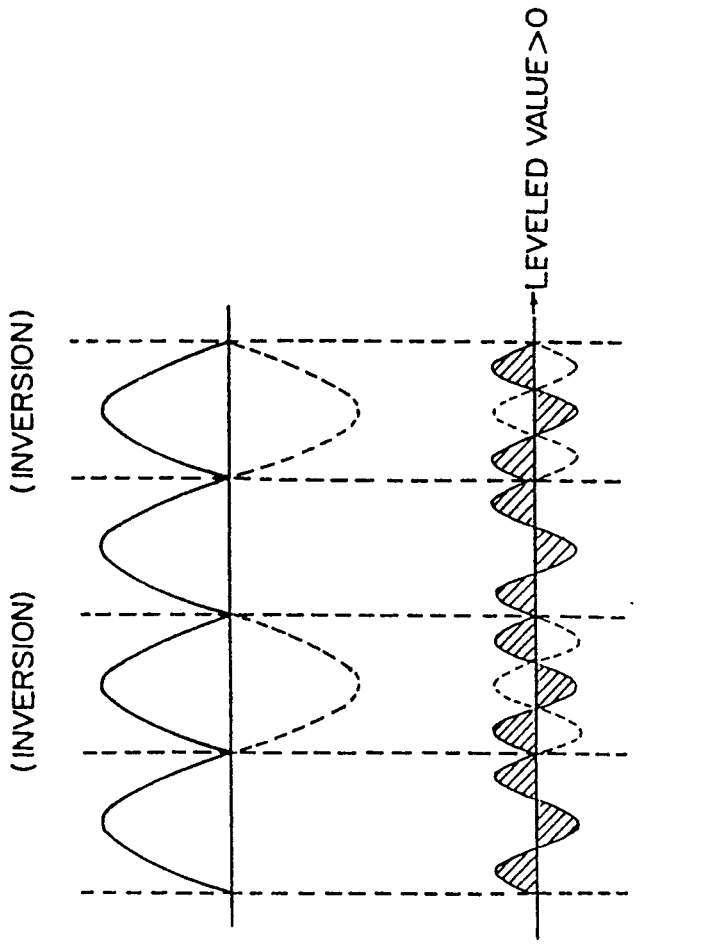

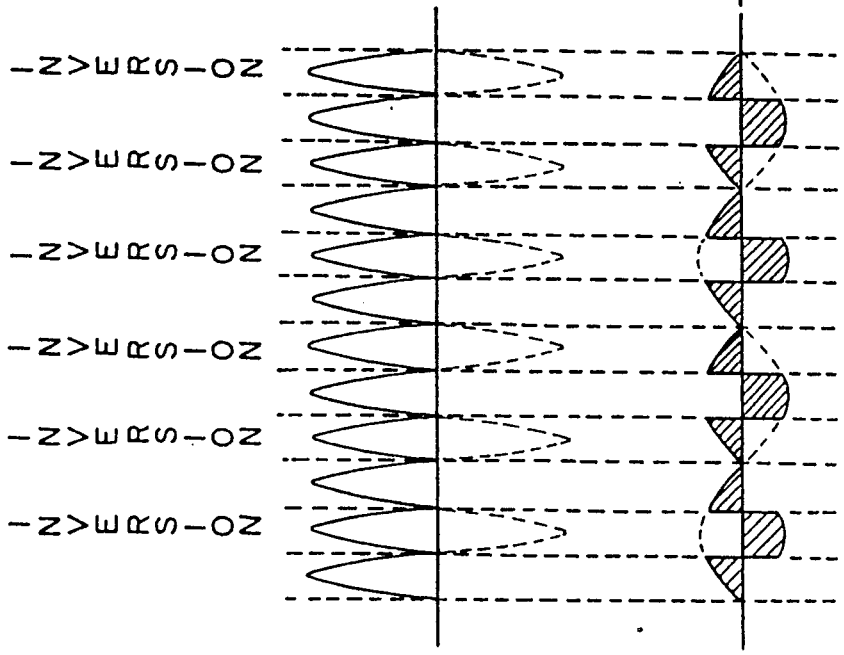

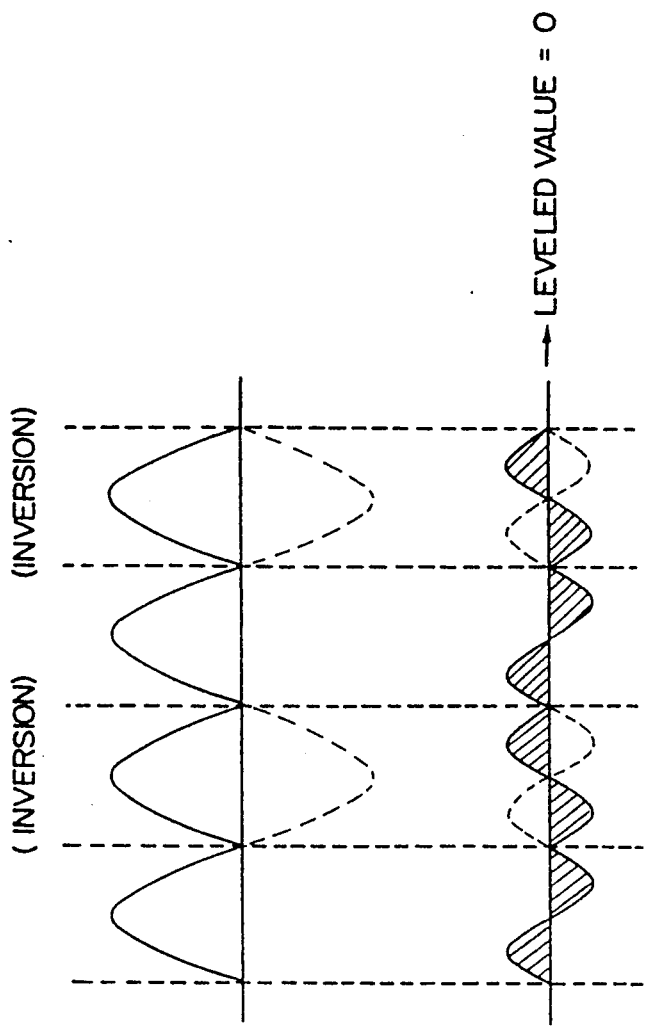

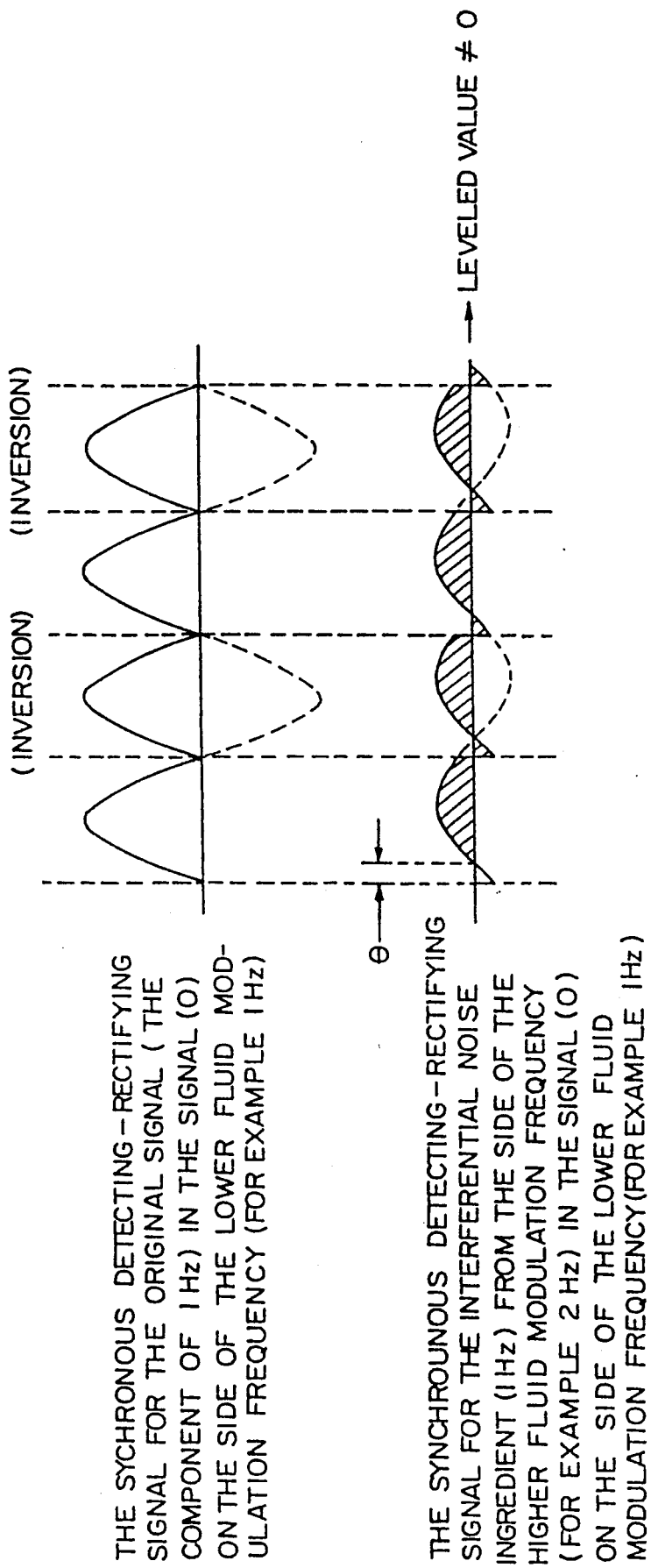

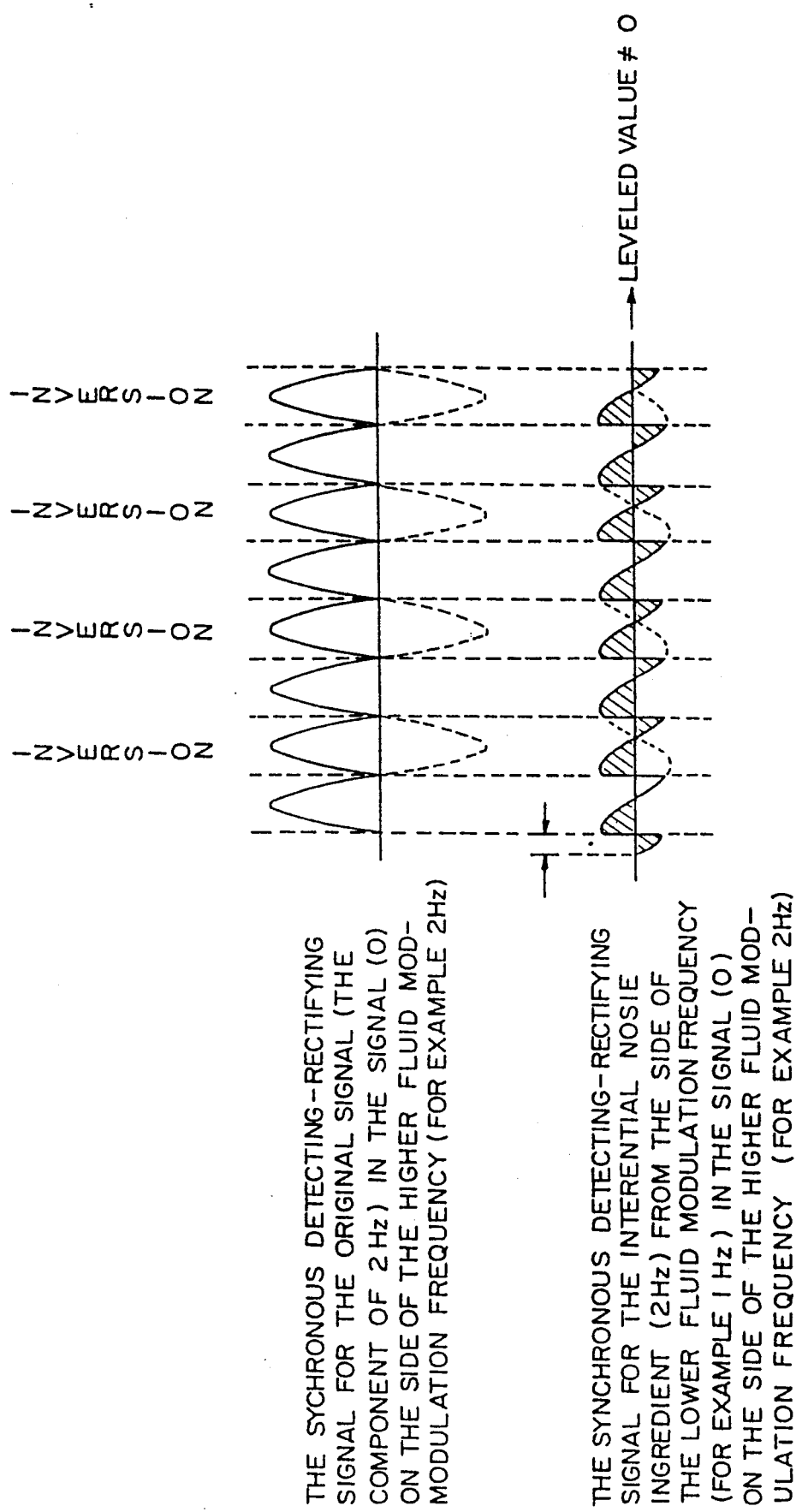

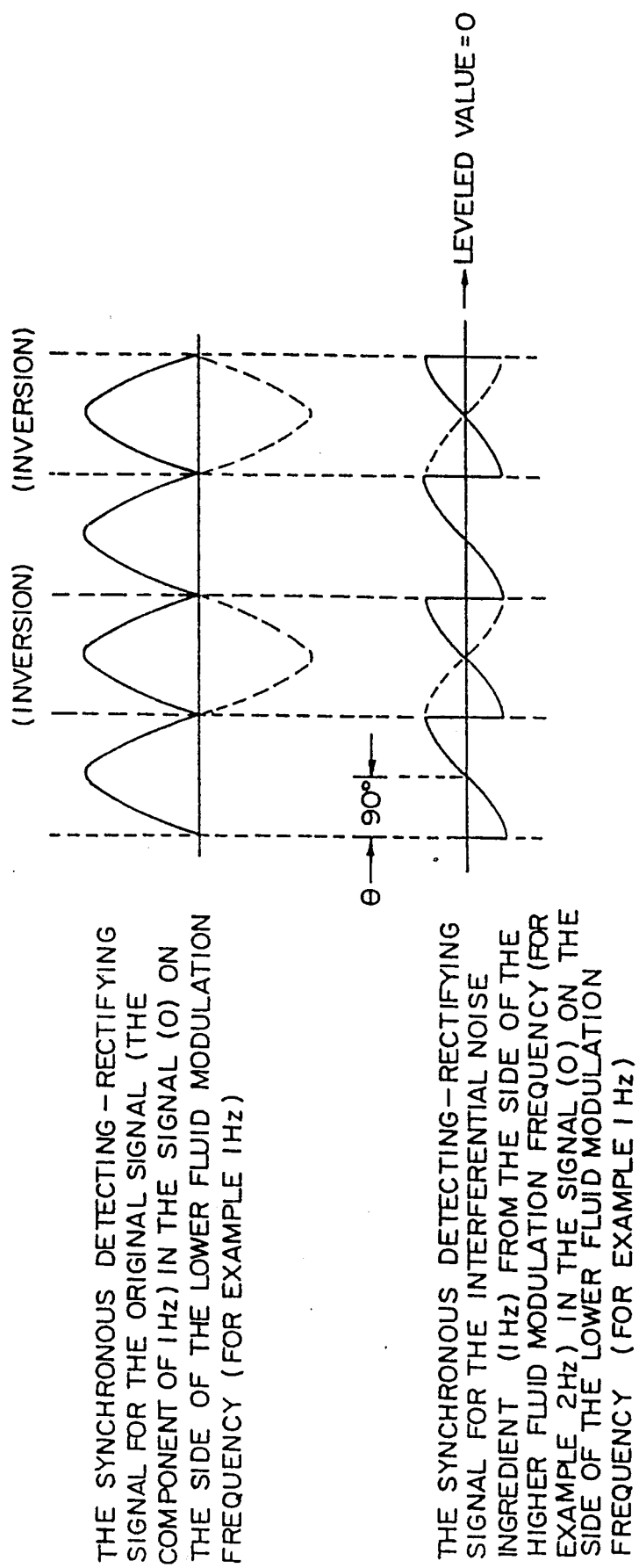

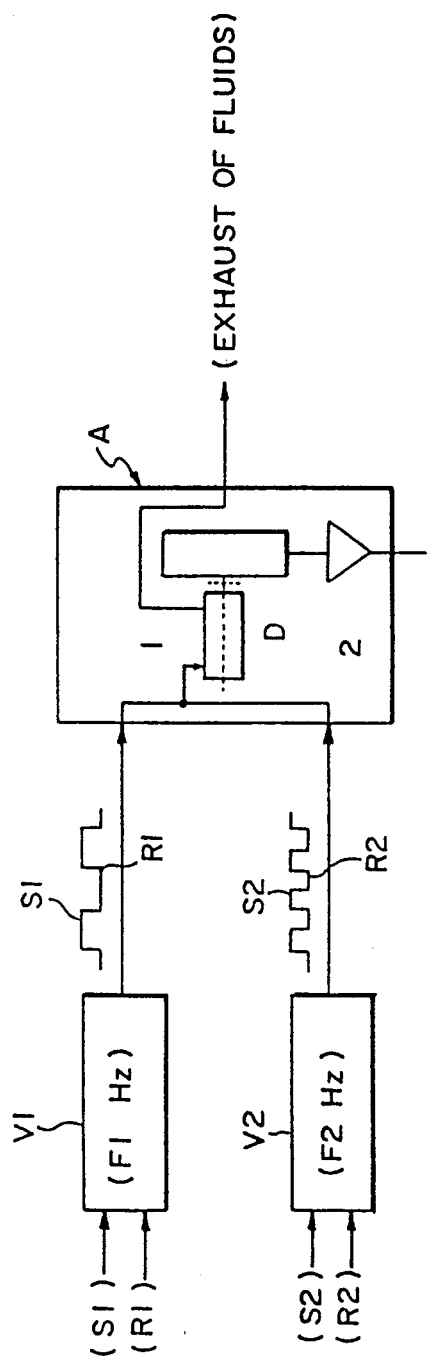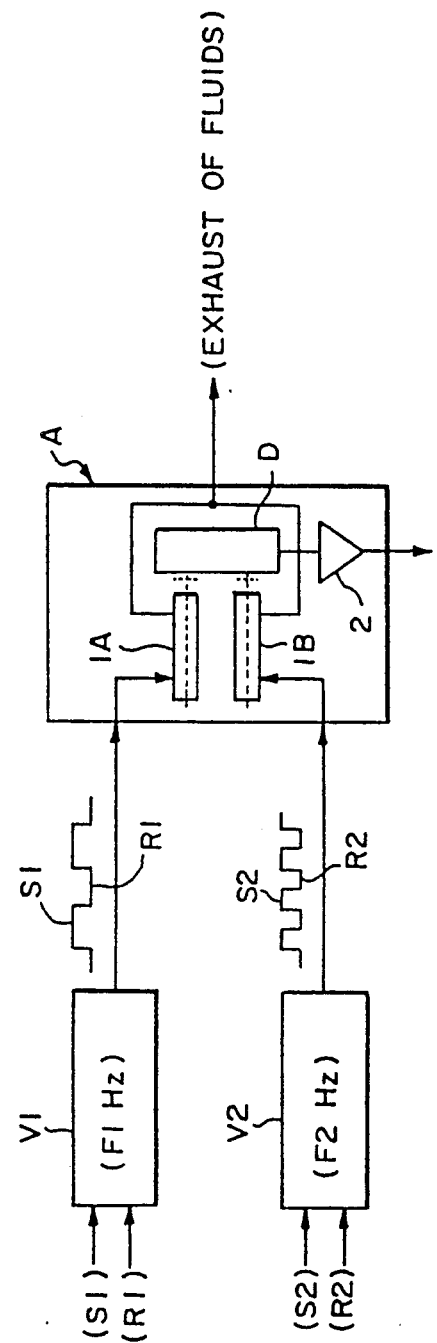

APPARATUS FOR ANALYZING FLUID BY MULTI-FLUID MODULATION MODE

This is a division of prior application Ser. No. 278,046, filed on Nov. 30, 1988, for a METHOD AND APPARATUS FOR ANALYZING FLUID BY MULTI-FLUID MODULATION MODE.

BACKGROUND OF THE INVENTION

1. Field of the Invention

The present invention relates to a novel method and apparatus for simultaneously and continuously analyzing a plurality of sample fluids using only one detector by a multi-fluid modulation mode (this is a name given by the present inventors).

2. Description of the Prior Art

Methods and apparatuses in which a fluid analyzer adopting various kinds of sensors is used, such as an analyzer provided with a chemical luminescence detector (CLD), an analyzer provided with a flame ion detector (FID), and a nondispersive type infrared analyzer (NDIR) provided with a pneumatic detector of condenser microphone sensor or microflow sensor or a solid detector such as a thermopile or semiconductor, have been known for analyzing a concentration (and thus a quantity) of noxious ingredients (such as $NO_x$, $H_yC_z$ or $CO_x$) in an exhaust gas from cars and plants contained in an atmosphere as one example of a sample fluid.

However, where the fluid analysis is required to simultaneously and continuously measure concentrations of a plurality of ingredients (for example, two ingredients such as NO and $NO_2$, methane ($CH_4$) and HC other than methane (nonmethane hydrocarbon) (NMHC) or CO and $CO_2$) contained in the sample fluid, a plurality of sensors (in this case, two sensors) have been required.

In the case where NO and $NO_2$ are simultaneously and continuously measured, the sample fluid is divided into two measuring systems: a first NO sensor for measuring a concentration of NO contained in the sample gas being disposed in one system, and a second NO sensor for subjecting $NO_2$ contained in the sample gas to a treatment for turning $NO_2$ into NO and measuring a concentration of total NO formed in the treated fluid being disposed in the other system. That is, two NO sensors are required. The concentration of $NO_2$ is obtained as a difference between a value of the concentration of total NO detected by the second NO sensor and a value of the concentration of only NO detected by the first NO sensor. This procedure is called a differential method. In the case where methane and HC other than methane (NMHC) are simultaneously and continuously measured, the sample fluid is divided into two measuring systems: a first HC sensor for measuring a concentration of total HC (THC) contained in the sample fluid being disposed in one system, and a second HC sensor for subjecting HC other than methane contained in the sample fluid to a treatment for catalytically burning and removing HC other than methane and measuring a concentration of methane contained in the treated gas being disposed in the other system. That is, two HC sensors are required. Also in this case, the differential method is used; that is, NMHC is obtained as a difference between a value of the concentration of THC detected by the first HC sensor and a value of the concentration of methane detected by the second HC sensor. In the case where CO and $NO_2$ contained in the sample fluid are simultaneously and continuously measured, the sample fluid is divided into two measuring systems, a CO sensor being disposed in one system, and a $CO_2$ sensor being disposed in the other system; that is, two sensors are required.

It is obvious that a plurality of sensors are required in the case where a plurality of ingredients contained in the sample fluid are simultaneously and continuously analyzed by dividing the sensors among a plurality of systems, as above described. It is also required in the case where a specific ingredient contained in a plurality of different sample fluids is simultaneously and continuously analyzed.

3. Problems to be Solved by the Invention

However, the requirement of a plurality of sensors as in the conventional methods and apparatuses for the simultaneous and continuous analysis of a plurality of ingredients contained in one fluid or the simultaneous and continuous analysis of the specific ingredient contained in a plurality of different sample fluids, as above described, leads to various kinds of problems. Among other things, (a) the analyzer is large in size and the cost of production is high; (b) since the calibration, such as zero-span calibration, is required for each of the sensors, much time is taken for the measurement; and (c) in the case where the calibration of the sensors is insufficient and there is an error in zero-calibration and a difference in sensitivity among the sensors, a large error of measurement is brought about.

In order to avoid such problems, a so-called batch type analyzing method has been used, in which a plurality of ingredients contained in one sample fluid are alternately determined or a plurality of different sample fluids are alternately measured by the use of an analyzer provided with only one sensor. But in such case, simultaneous and continuous measurement cannot be achieved, so that a disadvantage occurs in that the measured data is discontinuous. In particular, in the case where the analysis is carried out by the use of the differential method, there is the possibility that the accuracy of measurement is greatly reduced. Accordingly, it leads to such a great sacrifice of analysis of a fluid that a batch type analyzing method is used for merely reducing a number of sensors, which is not the best approach.

The present invention was achieved in view of such matters, and thus it is an object of the present invention to provide a method and apparatus for simultaneously and continuously analyzing a plurality of sample fluids with high accuracy by the use of only one sensor.

SUMMARY OF THE INVENTION

In order to achieve the above-described objects, a method of analyzing fluid by a multi-fluid modulation mode according to a first embodiment is characterized by a procedure comprising the steps of subjecting a plurality of sample fluids S1, S2, . . . , Sn (these may be different or a single sample fluid may be divided into a plurality of systems) to a fluid modulation by reference fluids R1, R2, . . . , Rn at frequencies F1, F2, . . . , Fn (hertz), respectively; simultaneously and continuously supplying an analytical portion A provided with only one sensor D with the respective sample fluids S1, S2, . . . , Sn subjected to the fluid modulation; dividing an output signal O from the sensor D in the analytical portion A into signal components 01, 02, . . . , On of the respective modulation frequencies F1, F2, . . . , Fn for the respective sample fluids S1, S2, . . . , Sn to rectify and level, whereby obtaining analyzed values about the respective sample fluids S1, S2, ..., Sn is achieved.

As seen in FIG. 1, showing a basic concept, and in FIG. 2, showing a specific construction of principal parts, an apparatus for analyzing a fluid by a multi-fluid modulation mode according to a second embodiment comprises fluid modulation means V1, V2, ..., Vn for subjecting a plurality of sample fluids S1, S2, ..., Sn (these may be different or a single sample fluid may be divided into a plurality of systems) to a fluid modulation by reference fluids R1, R2, ..., Rn, respectively, at differing frequencies F1, F2, ..., Fn (hertz); an analytical portion A provided with only one detector D, to which the respective sample fluids S1, S2, ..., Sn (subjected to the fluid modulation) are simultaneously and continuously supplied; and signal treatment means B for dividing an output signal O from the detector D in the analytical portion A into signal ingredients O1, O2, ..., On having respective modulation frequencies F1, F2, ..., Fn for the respective sample fluids S1, S2, ..., Sn by means of a suitable frequency-dividing means and a suitable signal-rectifying and levelling means (shown in FIG. 1) to carry out the rectification and the levelling treatment. Thereby, analytical values about the respective sample fluids S1, S2, ..., Sn are obtained and the signal treatment means B comprising a plurality of band-pass filters a1, a2, ..., an disposed in parallel to each other pass only signals within bands in the vicinity of the respective modulation frequencies F1, F2, ..., Fn of the output signal O from the detector D. A synchronous detector-rectifier b1 (b2, ..., bn) disposed in the lower streams of the respective band-pass filters A1 (a2, an) detect and rectify an output signal from the band-pass filter a1 (a2, ..., an) synchronously with the practical modulating action by the fluid modulation means V1 (V2, ..., Vn) corresponding to the frequency F1 (F2, ..., Fn) of the passband. A leveller element c1 (c2, ..., cn) disposed in the lower reaches of the respective synchronous detector-rectifiers b1 (b2, ..., bn) level an output signal from the respective synchronous detector-rectifiers b1 (b2, ..., bn), as specifically shown in FIG. 2.

An operation, which is exhibited by adopting such characteristic measures, is as follows:

In a method and apparatus for analyzing fluid by a multi-fluid modulation mode according to the present first and second embodiments, as still more obvious from the description of the preferred embodiments which will be mentioned later, a method is adopted in which a plurality of sample fluids S1, S2, ..., Sn are subjected to fluid modulation by the reference fluids R1, R2, ..., Rn at differing frequencies F1, F2, ..., Fn by the use of a suitable fluid modulation means V1, V2, ..., Vn composed of, for example, a rotary valve, three-way change over electromagnetic valve or four-way change over electromagnetic valve). The fluids are simultaneously and continuously supplied to the analytical portion A provided with only one sensor D to obtain one measured signal O (=O1+O2+...+On) comprising individual measured signal components (O1, O2, ..., On) corresponding to all sample fluids S1, S2, ..., Sn from only one sensor D. The signal treatment to rectify and level, in which the output signal O from the one sensor D is divided into the signal components O1, O2, ..., On of the respective modulation frequencies F1, F2, ..., Fn for said respective sample fluids S1, S2, ..., Sn, is carried out by the use of suitable signal treatment means B comprising a frequency-dividing circuit and a signal-rectifying and levelling circuit in combination, as shown in FIG. 1, to obtain the analyzed values about the respective sample fluids S1, S2, ..., Sn. Thus, the use of a simple and inexpensive analyzer provided with only one sensor is sufficient even in the simultaneous and continuous analysis of a plurality of ingredients in one sample fluid or the simultaneous and continuous analysis of one ingredient contained in a plurality of different sample fluids. Accordingly, the measurement system can be easily reduced in size and simplified and the cost can be easily reduced in comparison with the conventional method of analyzing a fluid. Furthermore, an error in zero-calibration between a plurality of sensors and a difference in sensitivity between a plurality of sensors are not produced as in the conventional methods and the regulation of the sensor can be easily carried out in a short time, so that an excellent accuracy of measurement can be secured.

Also, various kinds of soft or hard suitable means, such as a computer capable of operating Fourier analysis (corresponding to a frequency-dividing treatment) and digital analysis, such as an absolute value-averaging treatment (corresponding to a rectifying and levelling treatment) or an electric circuit such as a lock-in amplifier, can be used as the signal treatment means B. In the apparatus according to the present second embodiment, a plurality of signal treatment systems comprising the band-pass filters a1 (a2, ..., an), the synchronous detector-rectifiers b1 (b2, ..., bn) and the leveller elements (for example, low pass filters or condensers) c1 (c2, ..., cn) connected to each other in series are disposed in parallel, so that the apparatus can be remarkably simplified and inexpensive in comparison to the methods using the above-described computer or lock-in amplifier. In addition, an advantage occurs in that the apparatus is adapted to make up for the dividing action (for which there is the possibility that the use of merely the band-pass filters a1 (a2, ..., an) is insufficient) by the use of the synchronous detector-rectifiers b1 (b2, ..., bn) to carry out the division having a still higher accuracy, so that the signal treatment capacity (S/N ratio) is remarkably superior to the apparatus having a construction wherein the frequency is divided merely by the band-pass filter and then immediately the absolute value rectification is carried out.

BRIEF DESCRIPTION OF THE DRAWINGS

FIG. 2 is a block diagram showing principal parts in the apparatus according to the present second embodiment; and Various kinds of preferred embodiments of the method and apparatus according to the present invention are shown in FIGS. 3 to 27, in which:

Figure 13:
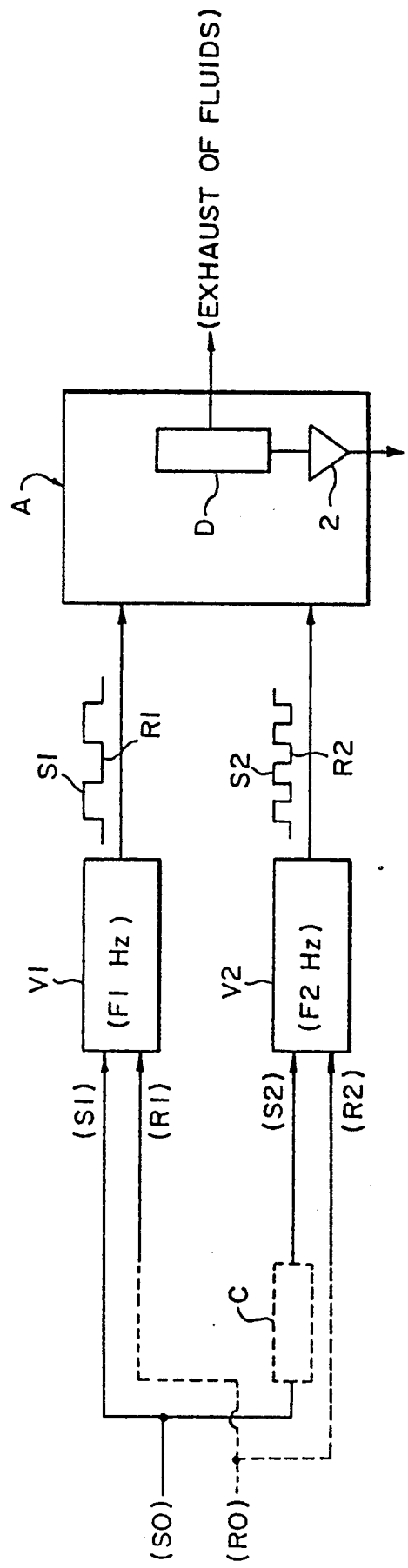
Figure 14:
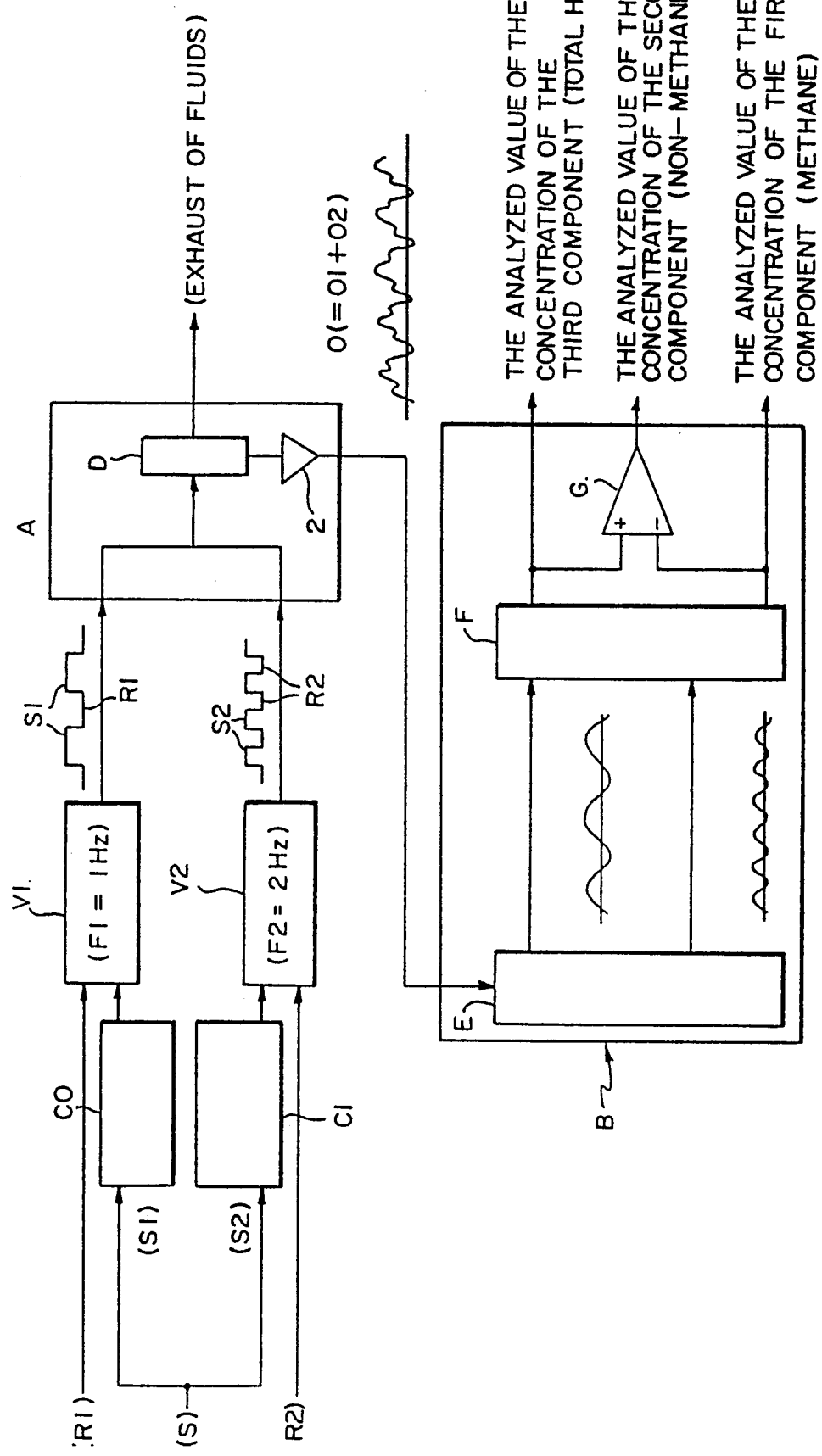
Figure 15:
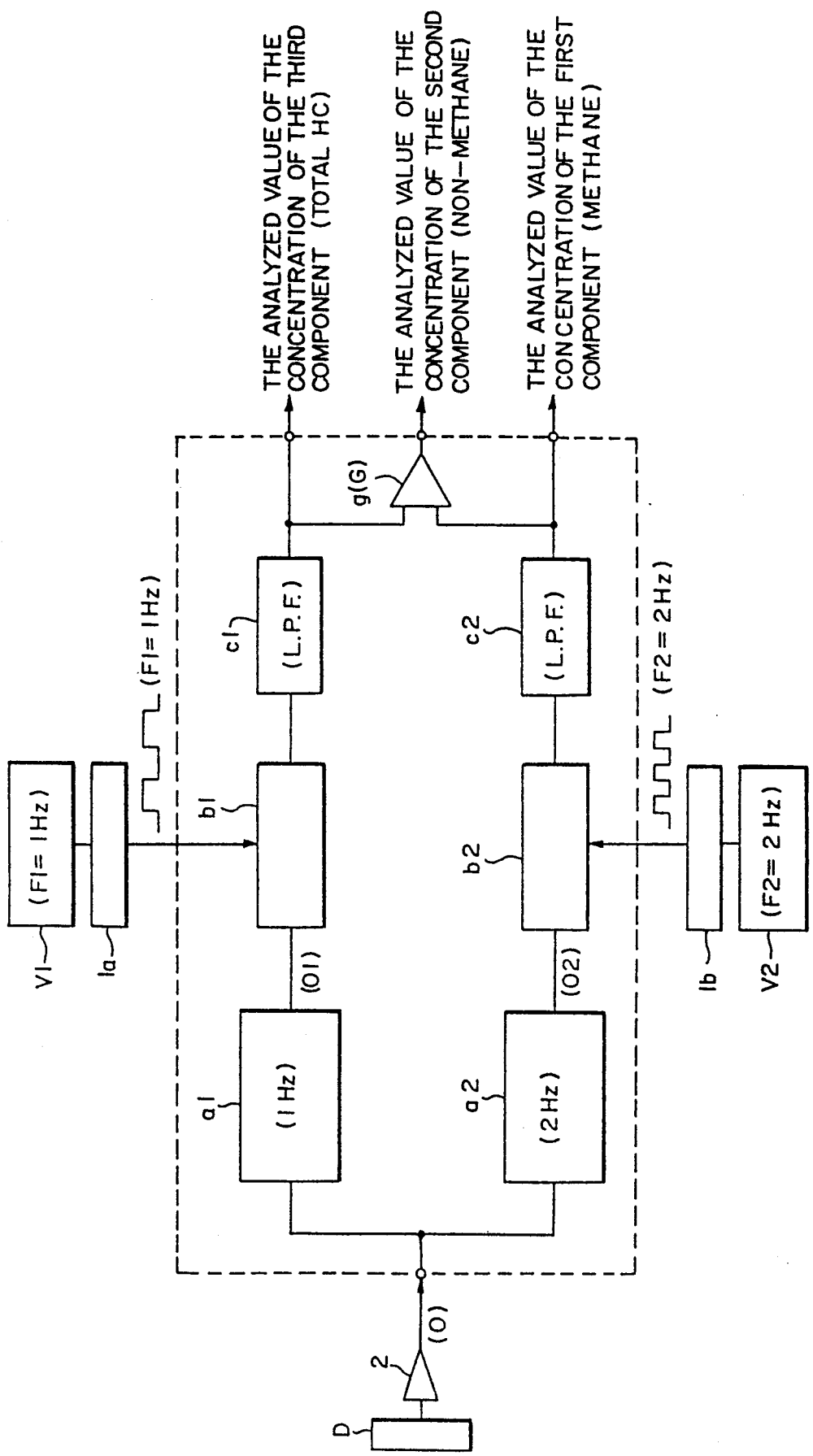
Figure 16:
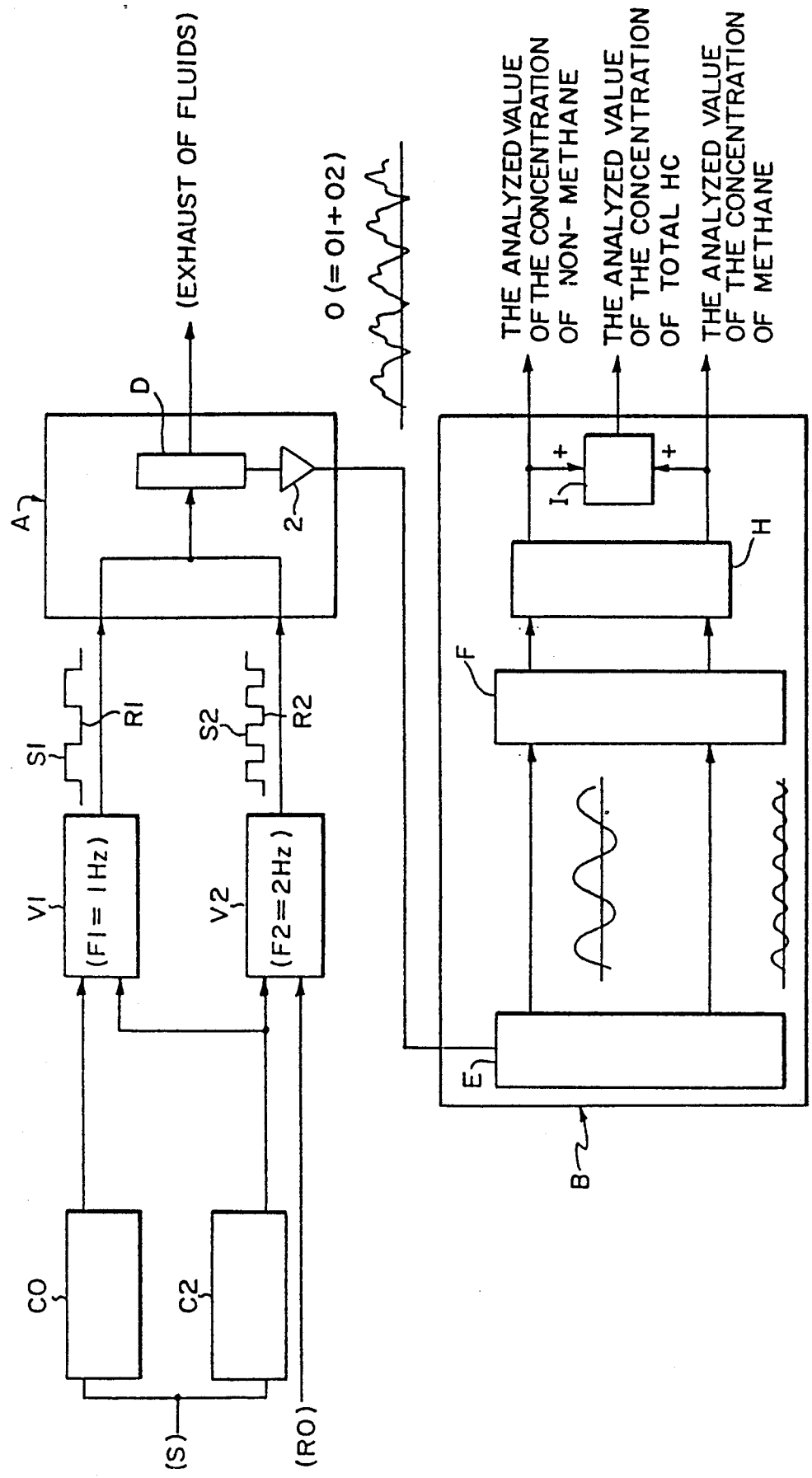
Figure 17:
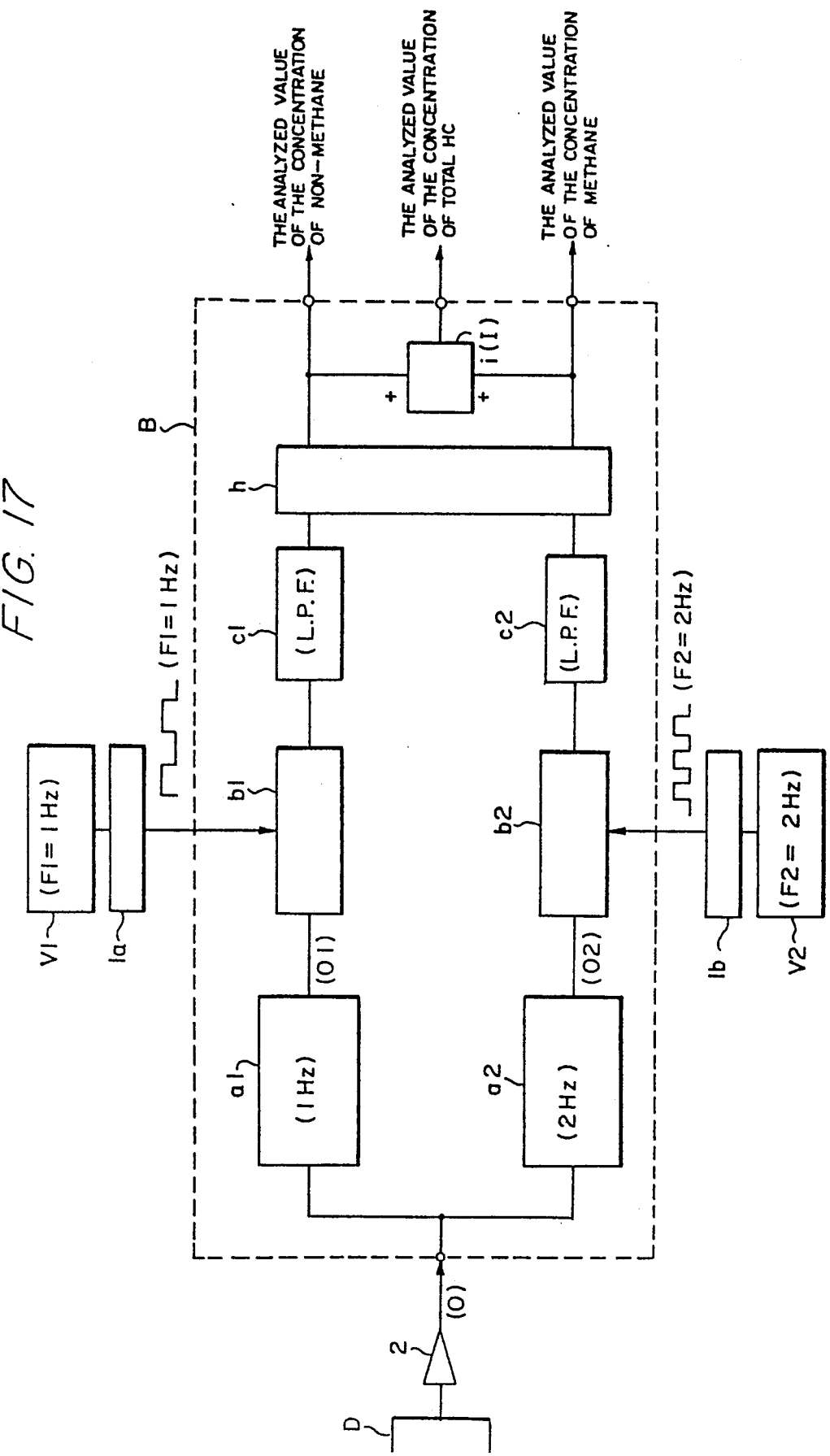
Figure 18:
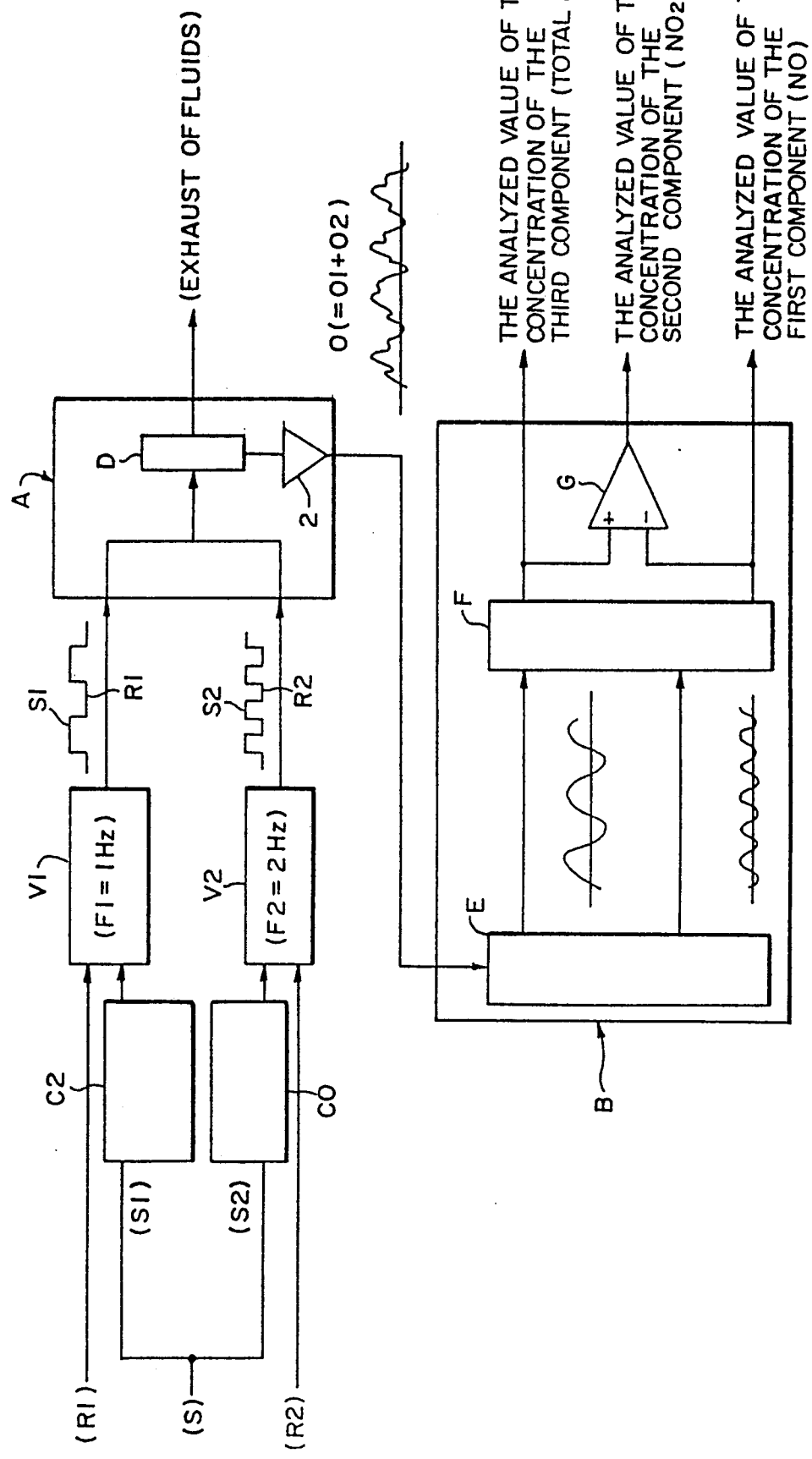
Figure 19:
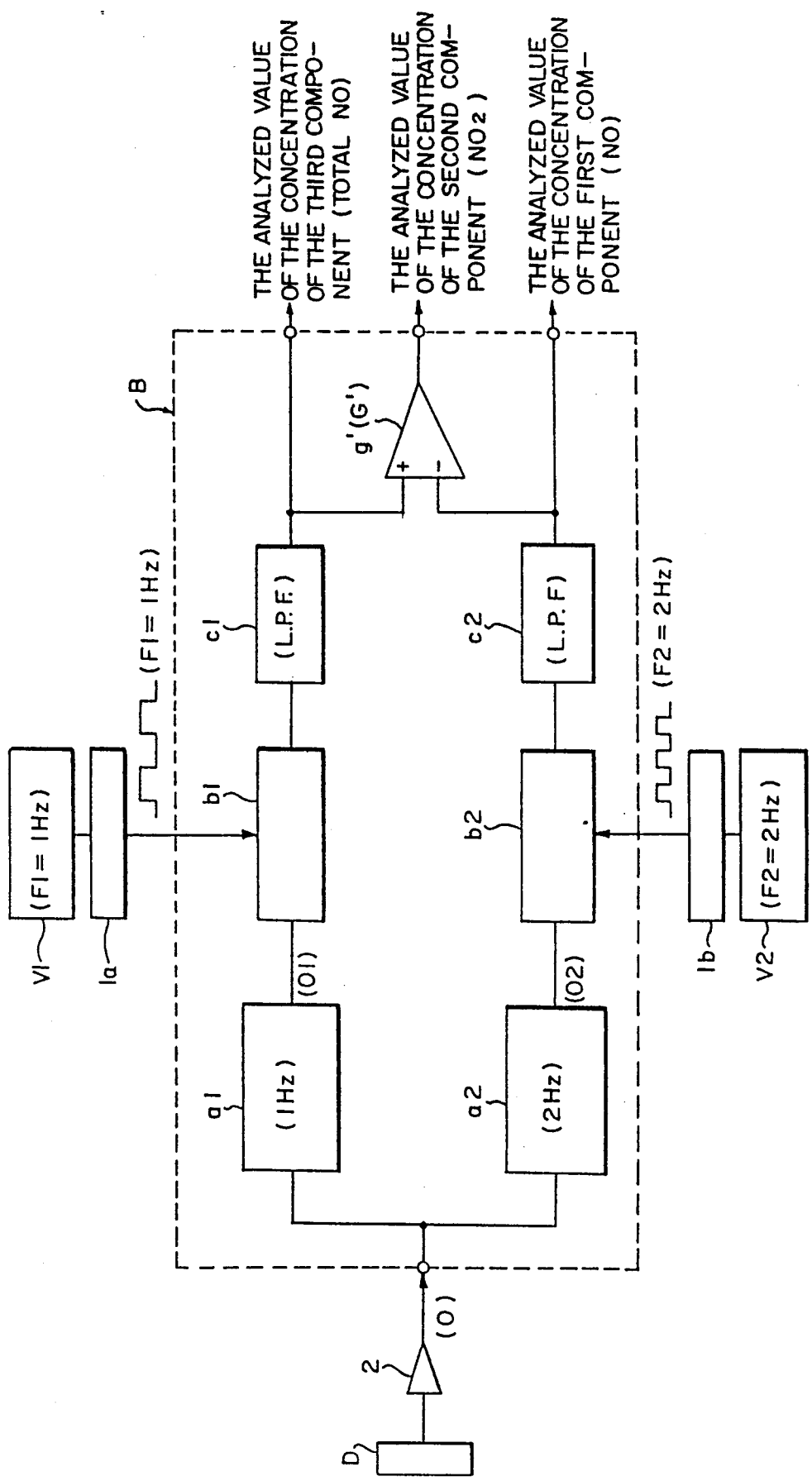
Figure 20:
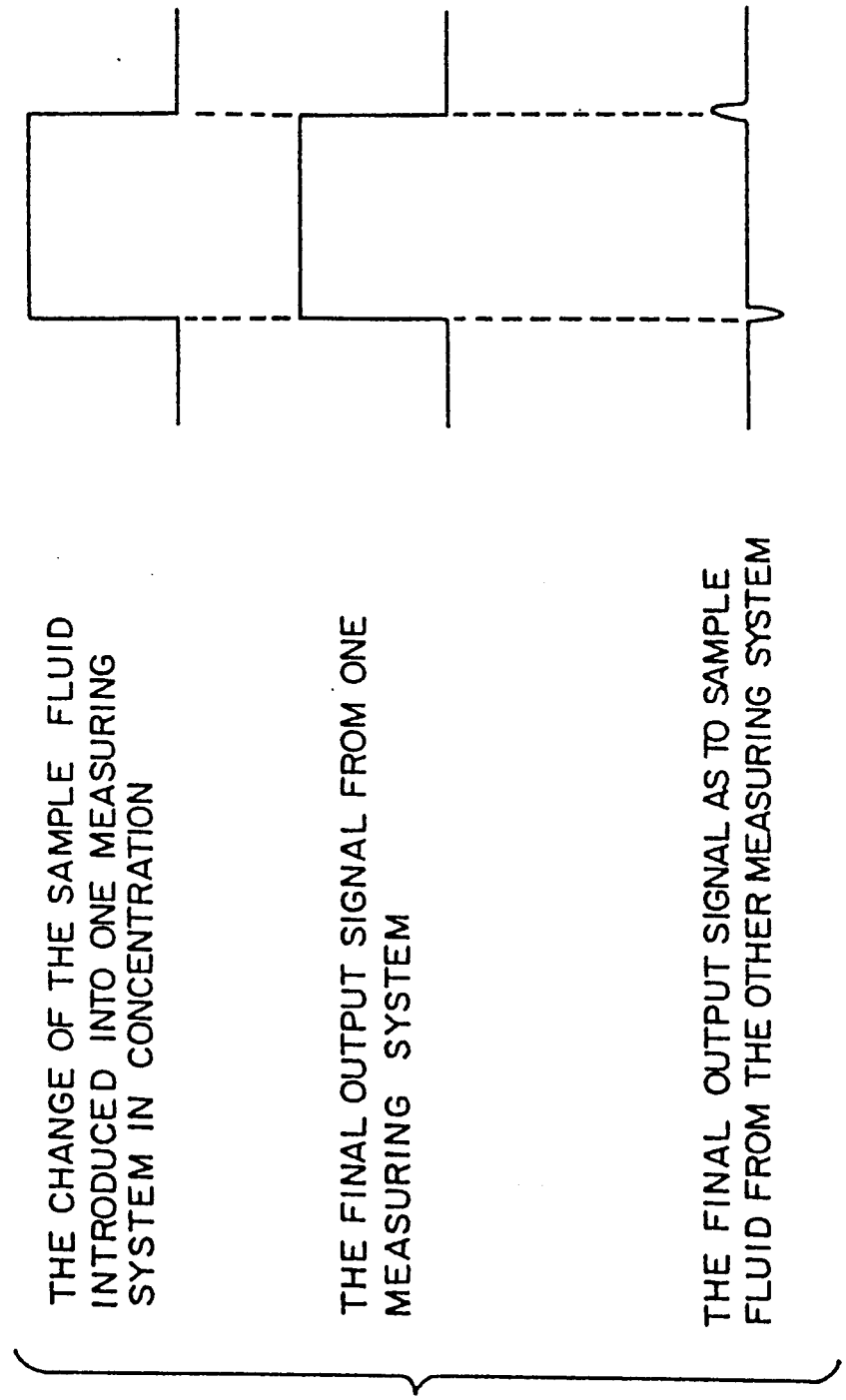
Figure 21:
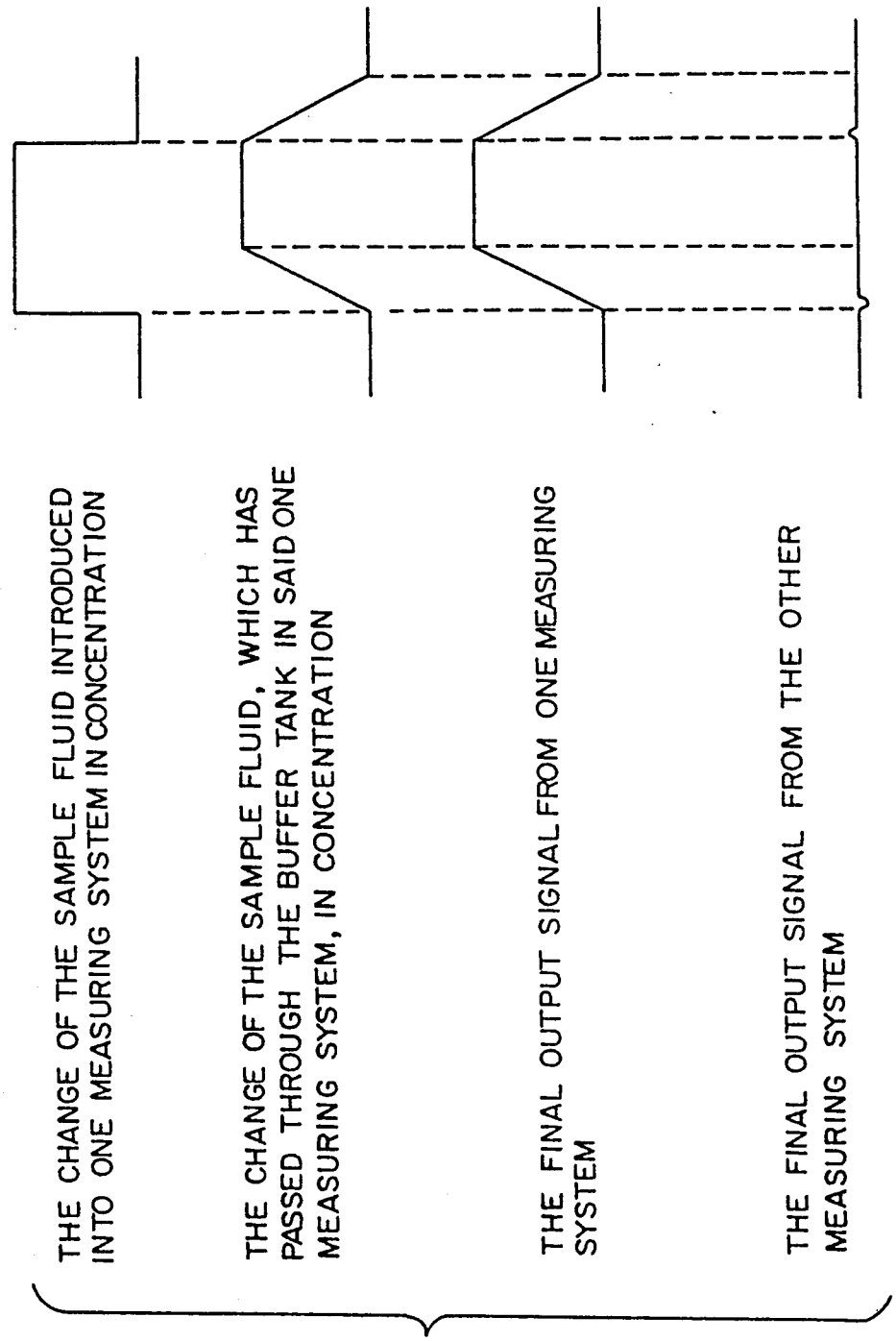
Figure 22:
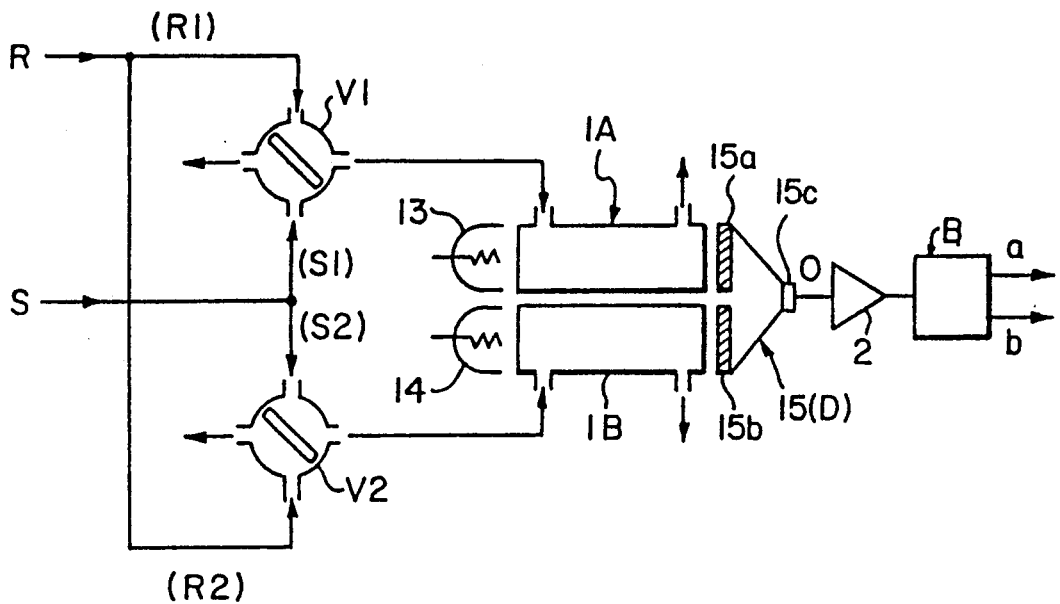
Figure 23:
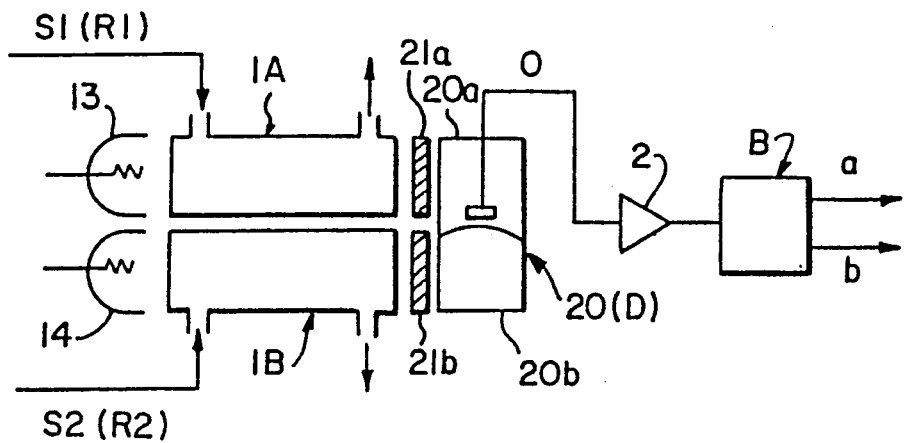
Figure 24:
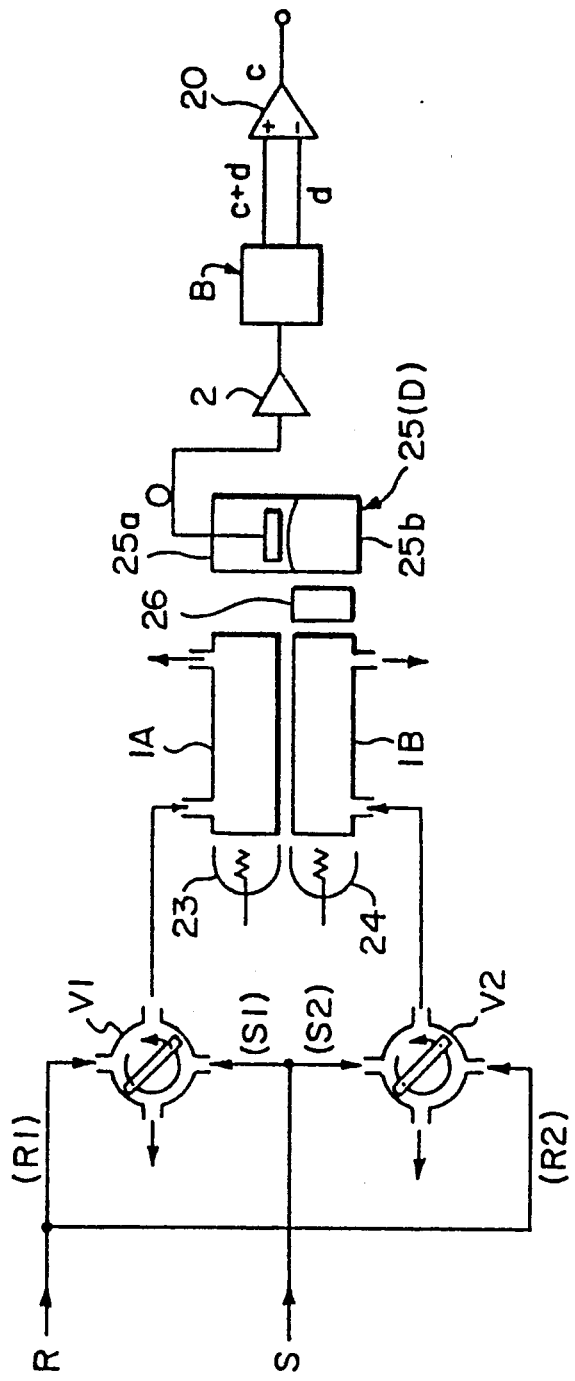
Figure 25:
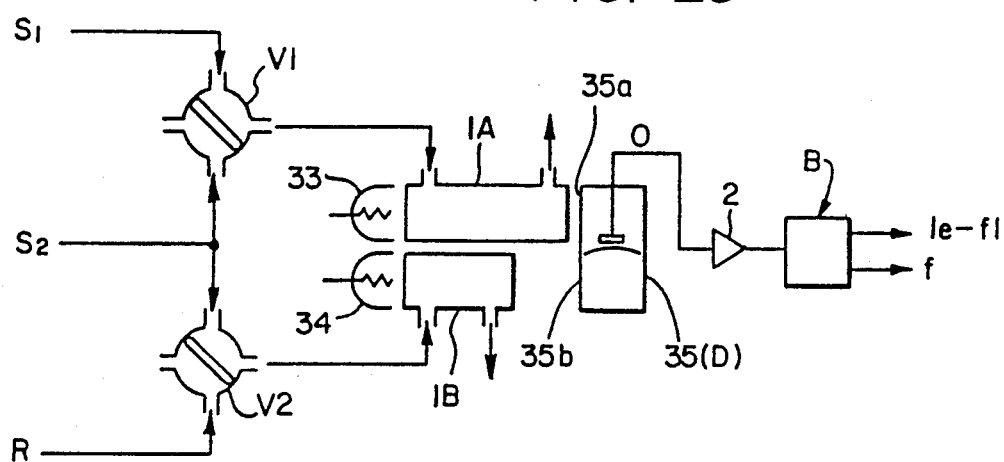
Figure 26:
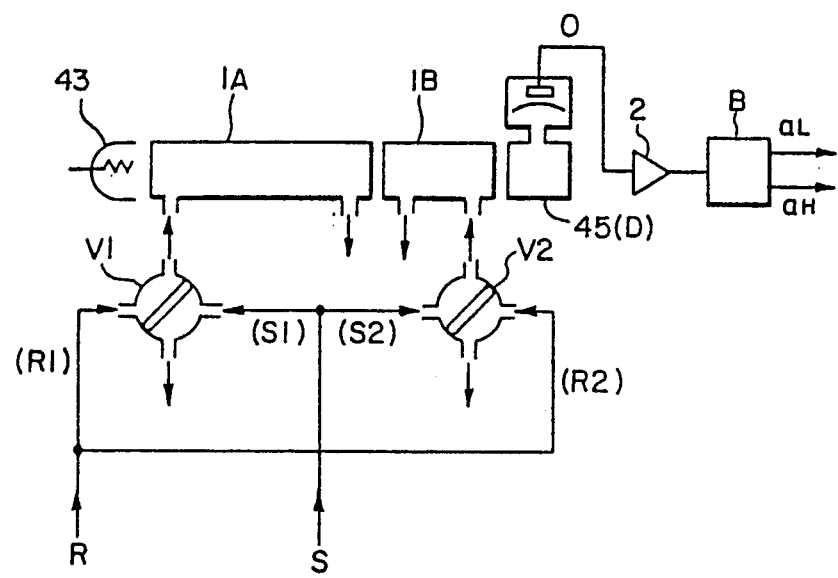
Figure 27:
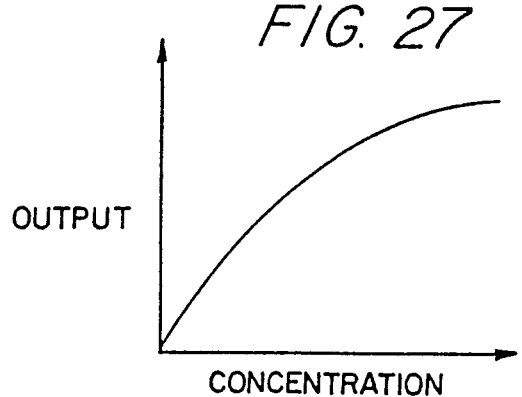

FIG. (6), 6a-b; FIG. (7), 7a-7d and FIG. (8) 8(A), 8(b) are diagrams showing a detailed operation of the signal treatment means and fluid modulation means, respectively;

FIG. (9) 9(A)-9(B) is a detailed block diagram showing the fluid modulation means;

FIG. (10) 10(A)-10(B) is a diagram showing an operation by the fluid modulation means;

FIG. 11 is a block diagram showing principal parts of an apparatus according to a second basic preferred embodiment;

FIG. 12 is a block diagram showing principal parts of an apparatus according to a third basic preferred embodiment;

FIG. 13 is a block diagram showing principal parts of modifications of the apparatus according to the above described first to third basic preferred embodiments;

FIG. 14 is a general block diagram showing an apparatus according to a first applied preferred embodiment;

FIG. 15 is a block circuit diagram showing signal treatment means which is a principal part of the apparatus according to the first applied preferred embodiment;

FIG. 16 is a general block diagram showing an apparatus according to a second applied preferred embodiment;

FIG. 17 is a block circuit diagram showing signal treatment means which is a principal part of the apparatus according to the second applied preferred embodiment;

FIG. 18 is a general block diagram showing an apparatus according to a third applied preferred embodiment;

FIG. 19 is a block circuit diagram showing signal treatment means which is a principal part of the apparatus according to the third applied preferred embodiment;

FIG. 20 is a diagram showing a detailed operation of the above-described first to third applied preferred embodiments;

FIG. 21 is a diagram showing a detailed operation of the above-described first to third applied preferred embodiments;

FIG. 22 is a general block diagram showing an apparatus according to a fourth applied preferred embodiment;

FIG. 23 is a block diagram showing principal parts of an apparatus according to a modification of the fourth applied preferred embodiment;

FIG. 24 is a general block diagram showing an apparatus according to a fifth applied preferred embodiment;

FIG. 25 is a general block diagram showing an apparatus according to a sixth applied preferred embodiment;

FIG. 26 is a general block diagram showing an apparatus according to a seventh applied preferred embodiment; and FIG. 27 is a diagram showing concentration-output characteristics of a general absorption analyzer used for describing an operation of the apparatus according to the seventh applied preferred embodiment.

DETAILED DESCRIPTION OF THE PREFERRED EMBODIMENTS

The preferred embodiments of a method and apparatus for analyzing fluid by a multi-fluid modulation mode according to the present invention are described below with reference to the drawings (FIGS. 3 to 27).

Figure 1:
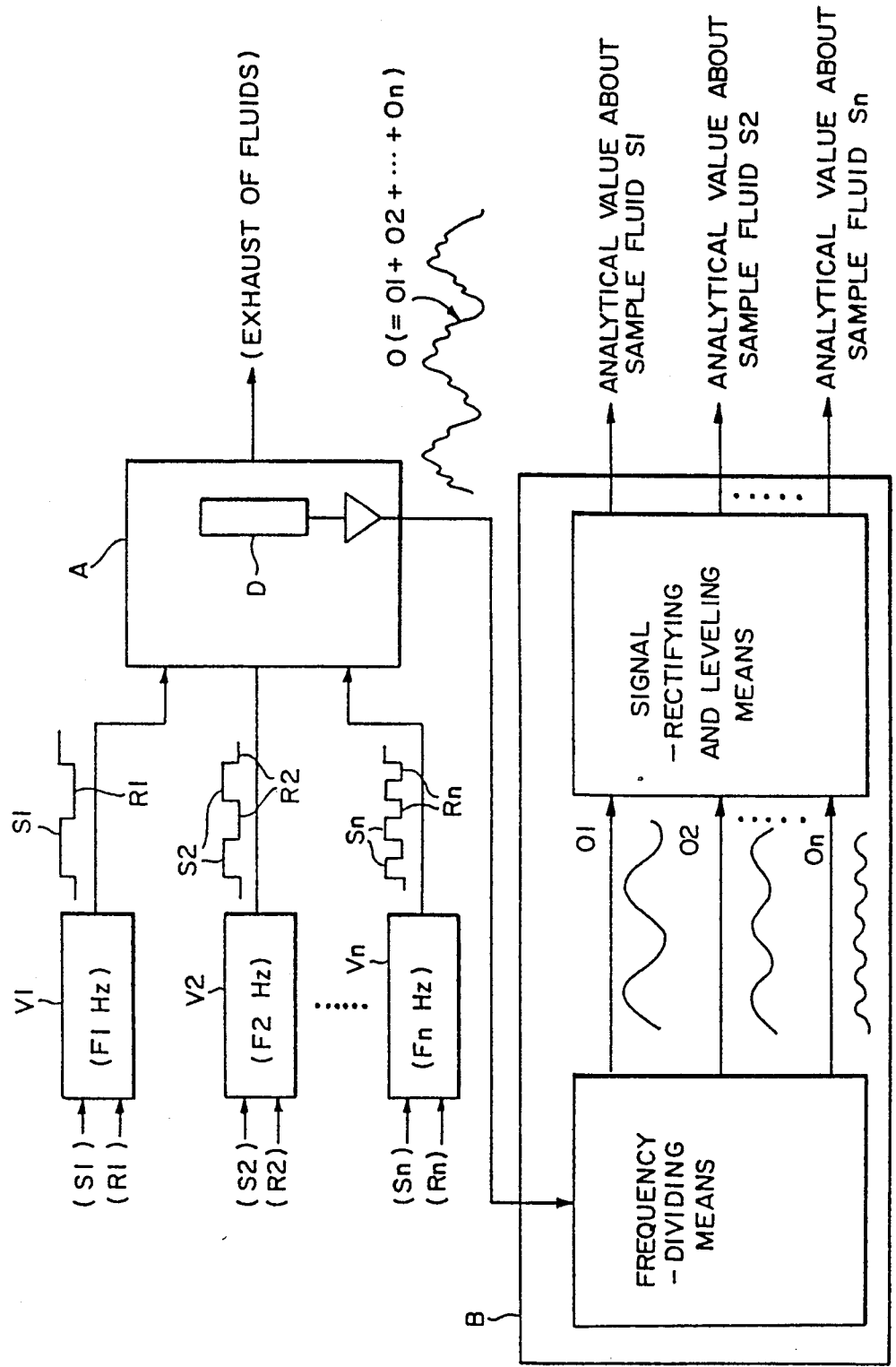
FIG. 1 is a diagram showing a basic concept and an operation of a method of analyzing a fluid by a multi-fluid modulation mode and an apparatus for carrying out the same according to the present first and second embodiments.
Figure 2:
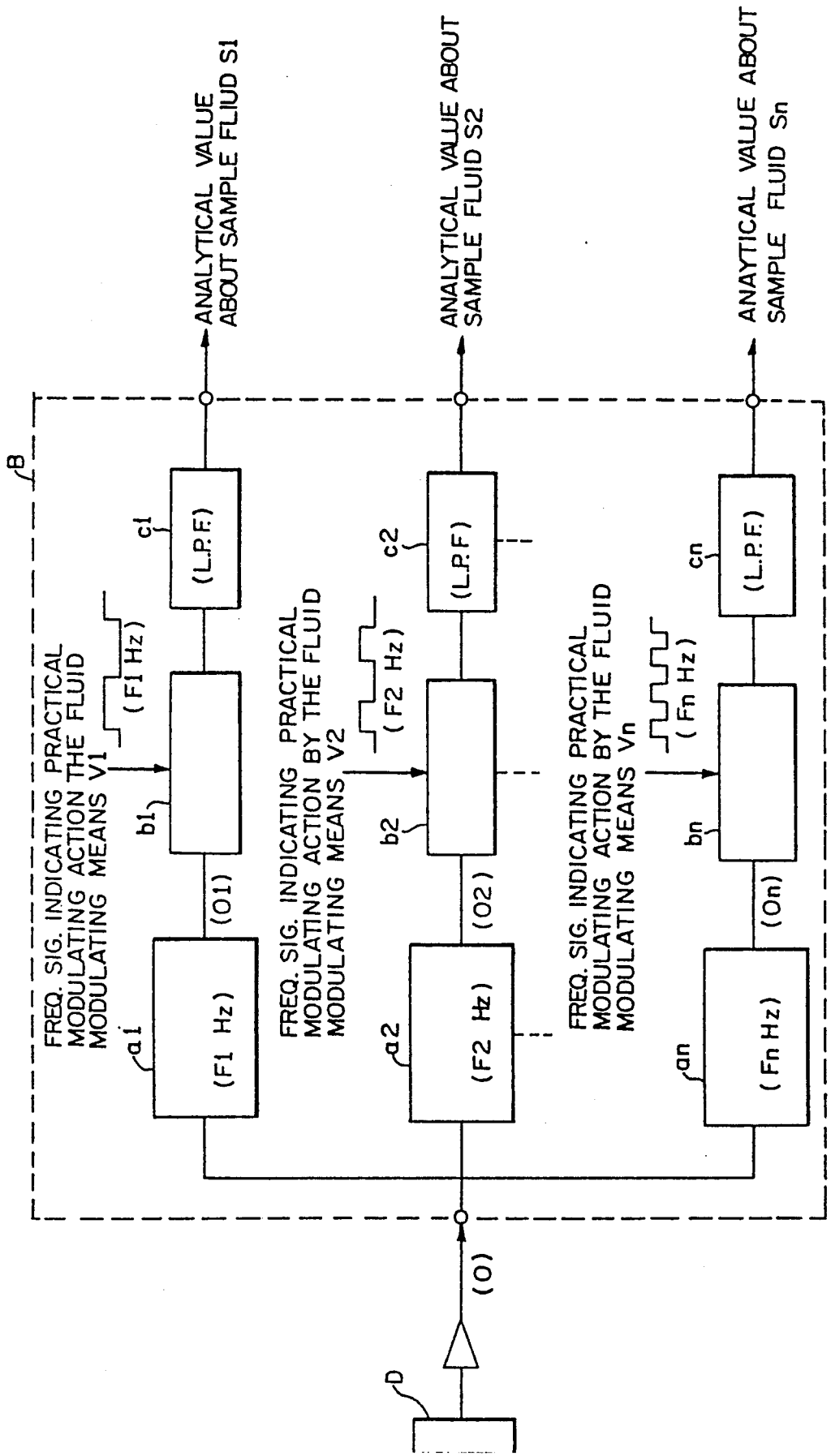
Figure 3:
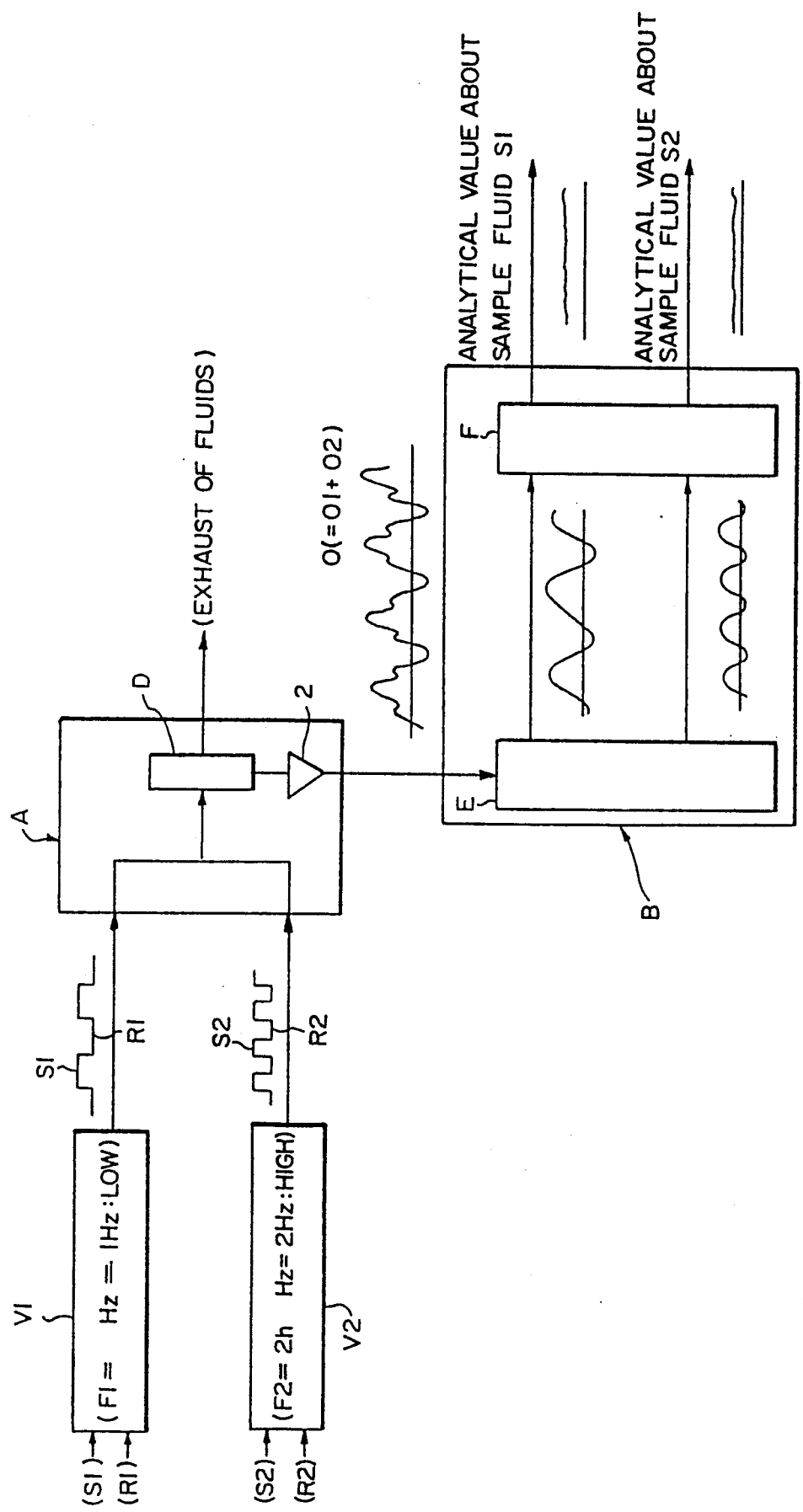
FIG. 3 is a general block diagram showing the apparatus according to a first basic preferred embodiment.

FIG. 3 relates to a first basic preferred embodiment and shows a construction of a system for analyzing fluid by a multi-fluid modulation mode according to the present invention where the concentration of $NO_x$, $H_yC_z$ or the like contained in the sample fluid (such as an exhaust fluid from plants and the atmosphere) is determined.

As shown, a plurality (in this case, two) of sample fluids S1, S2 (these may be originally different or a single sample fluid divided into a plurality of systems, as mentioned later) are subjected to a fluid modulation by reference fluids R1, R2 (in general a zero gas is used) at frequencies F1, F2 (hertz) differing from each other by the use of fluid modulation means V1, V2, respectively. In short, the sample fluids and the reference fluids are alternately passed through and then the respective sample fluids S1, S2, which have been subjected to the fluid modulation by the reference fluids R1, R2 are simultaneously and continuously supplied to the analytical portion A provided with only one sensor D.

In addition, both fluid modulation means V1, V2 are set so that the ratio of the fluid modulation frequencies F1, F2 may be even numbers or reciprocals thereof. In short, they are set so that the other frequency (F2 or F1) may be 2xhlHz (h is an integer) when one frequency (F1 or F2) is 1Hz. In the preferred embodiment F1=1 Hz for sample fluid S1 of high concentration and F2=2 Hz for sample fluid S2 of low concentration (l=1, h=1) to provide a characteristic frequency for each sample portion. In addition, in this case, a chemical luminescence detector (CLD) for use in the detection of NO, a flame ion detector (FID) for use in the detection of hydrocarbons (HC) and the like, in short, detectors of several types, through which the sample fluid directly passes, are used as the sensor D in the analytical portion A, so that both sample fluids S1, S2, which have been subjected to the fluid modulation, are supplied to the sensor D under a mixed condition.

Accordingly, the signal O output from the sensor D through the preamplifier 2, as schematically shown in the drawings, is obtained in the form of one measured signal (O=O1+O2) comprising the individual measured signal components (O1, O2) corresponding to both sample fluids S1, S2 in the aggregate.

Therefore, the output signal O from the sensor D is subjected to a signal treatment to rectify and level, in which it is divided into the signal components O1, O2 of the respective modulation frequencies F1 (1 Hz), F2 (2 Hz) for the respective sample fluids S1, S2 by the use of suitable signal treatment means B such as an electric circuit comprising the frequency-dividing circuit E and the signal-rectifying and levelling circuit F in combination, as conceptionally shown in FIG. 3, whereby the analyzed values about the respective sample fluids S1, S2 are obtained.

Figure 4:
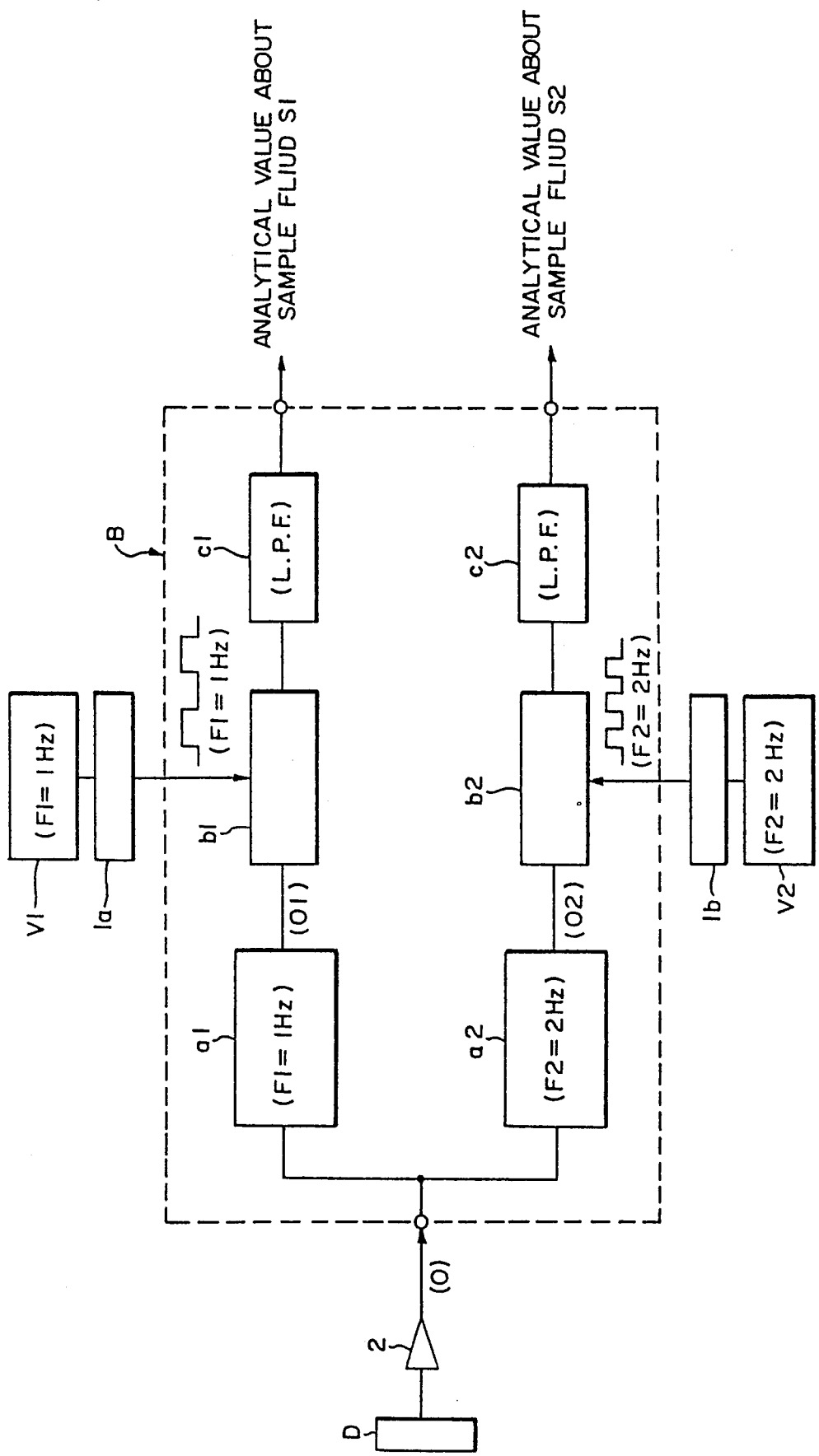
FIG. 4 is a block circuit diagram showing signal treatment means, which is a principal part of the apparatus according to the first basic preferred embodiment.

The specific circuit construction of the signal treatment means B is shown in FIG. 4. The signal O output from the detector D through the preamplifier 2 is branched into a plurality of signal treatment systems (in this example, two systems) disposed in parallel to each other. A band-pass filter a1 for dividedly taking out only the signal O1 having the modulation frequency F1 (1 Hz) for the sample fluid S1 (making only the signal O1 having the modulation frequency F1 [1 Hz] for the sample fluid S1 pass therethrough) is disposed in one signal treatment system. The synchronous detector-rectifier b1 for synchronously rectifying the output signal O1 from the band-pass filter a1 is disposed in the lower reaches of the band-pass filter a1 so as to make up for the frequency-dividing action, for which there is the possibility that the use of merely the band-pass filter a1 is insufficient, by the use of the synchronous signal (signal expressing the actual fluid-modulating action by the fluid modulation means V1: F1=1 Hz) from a synchronous signal generator 1a mounted on the fluid modulation means V1 for the sample fluid S1. Thereby, carrying out the division having a still higher accuracy is achieved, and simultaneously converting the divided alternating current into a direct current is provided. The low pass filter (L.P.F.) as the leveller element c1 levels the output signal from the synchronous detector-rectifier b1 and removes high-frequency noises while being disposed in the lower reaches of the synchronous detector-rectifier b1. The band-pass filter a2 dividedly takes out only the signal O2 having the modulation frequency F2 (2 Hz) for the sample fluid S2 (making only signal O2 having the modulation frequency F2 [2 Hz] for the sample fluid S2 pass therethrough) and is disposed in one signal treatment system. The synchronous detector-rectifier b2 synchronously rectifies the output signal O2 from the band-pass filter a2 which is disposed in the lower reaches of the band-pass filter a2 so as to make up for the frequency-dividing action, for which there is the possibility that the use of merely the band-pass filter a2 is insufficient, by the use of the synchronous signal (signal expressing the actual fluid-modulating action by the fluid modulation means V2: F2=2 Hz) from a synchronous signal generator mounted on the fluid modulation means V2 for the sample fluid S2. Thereby, carrying out the division having a still higher accuracy is achieved, and simultaneously converting the divided alternating current into a direct current is provided. The low pass filter (L.P.F.) as the leveller element c2 levels the output signal from the synchronous detector-rectifier b2 and removes high-frequency noises while being disposed in the lower reaches of the synchronous detector-rectifier b2. In addition, the signal treatment means B is not limited to hard means, such as the above-described electric circuits. Soft means, such as the computer system capable of operating Fourier analysis (corresponding to the frequency-dividing treatment) and the digital analysis, such as the absolute value-averaging treatment (corresponding to the rectifying and levelling treatment), may be used.

Figure 5A:
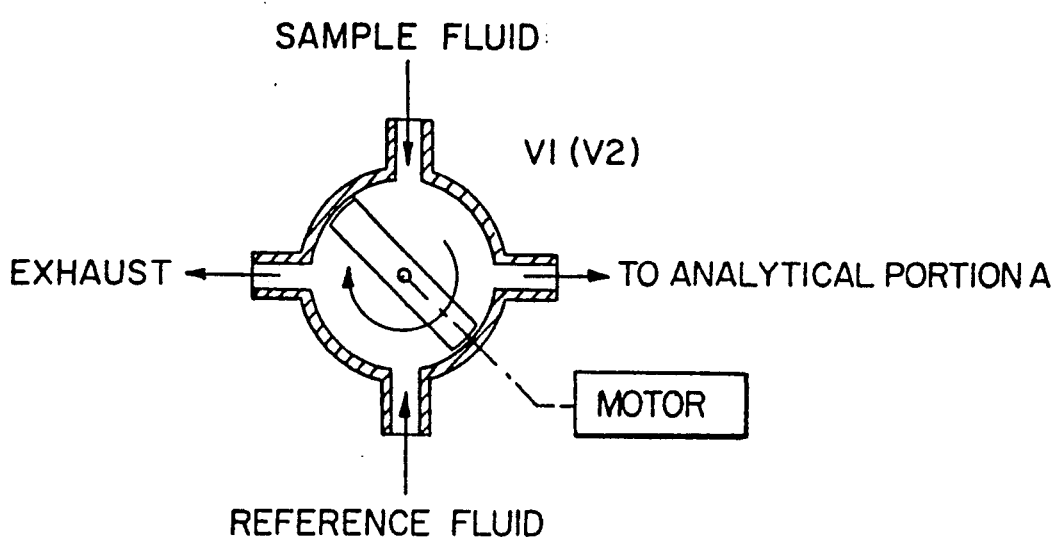
FIG. 5(A), 5(B) is a diagram showing fluid modulation means which is another principal part of the apparatus according to the first basic preferred embodiment.
Figure 5B:
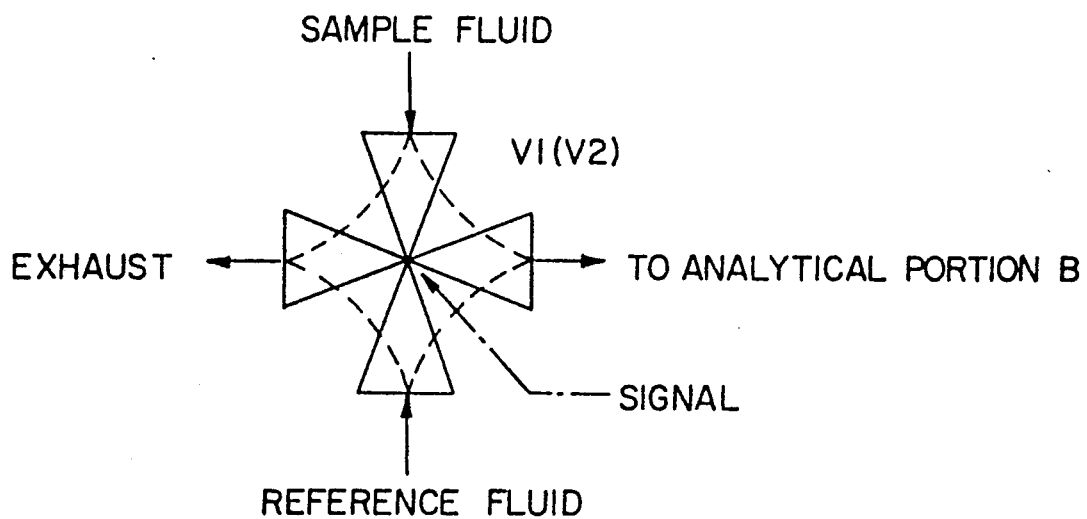

In addition, every means capable of alternately changing-over the sample fluid S1 (S2) and the reference fluid R1 (R2) at the appointed frequency of an optional construction can be used as the respective fluid modulation means V1, V2. For example, a rotary valve as shown in FIG. 5(A) may be used. Or, a four-way changing-over electromagnetic valve (not shown) may be used. Furthermore, a three-way changing-over electromagnetic value (not shown) may be used.

As an example in which the fluid modulation frequencies F1, F2 by both fluid modulation means V1, V2 are set at 1 Hz and 2 Hz, respectively, was shown in the above-described preferred embodiment, the reason for such setting is described below.

As described with reference to FIG. 4, in the signal treatment means B, the measured signal O from the sensor D is first divided into individual measured signal ingredients O1 (having a frequency of F1) and O2 (having a frequency of F2) corresponding to both sample fluids S1, S2 by means of the band-pass filters a1, a2. But so far as any practically very difficult measure is not taken (for example, when both fluid modulation frequencies F1, F2 are not greatly and differently set or high-grade band-pass filters having considerably sharp frequency-cutting characteristics are not used as both band-pass filters a1, a2), reliable division of frequency cannot be achieved, whereby the mutual interference, in which a noise ingredient due to the other fluid modulation frequency F2 (F1) is mixed in the signal, which passed through each band-pass filter a1 (a2), in addition to the signal O1 (O2) having the original frequency F1 (F2), cannot be avoided.

If the noise ingredient having the other fluid modulation frequency F2 (F1) due to the mutual interference is mixed in the signal, which passed through each band-pass filter a1 (a2) in the above-described manner, the following disadvantages occur:

Both fluid modulation frequencies F1, F2 can be optionally set as a rule, but in this case, as a rule, even after the signal was subjected to the synchronous detection-rectification by the synchronous detector-rectifier b1 (b2), the signal corresponding to the interferential noise ingredient remains as a factor for errors in measurement. In short, the levelled value of the signal does not amount to 0.

This will be easily understood from FIG. 6(A), (B) illustrating a case where, for example, one fluid modulation frequency F1 is set at 1 Hz and the other fluid modulation frequency F2 is set at 3 Hz.

In addition, it has been experimentally shown that there is a tendency that the factor for errors in measurement due to the above-described mutual interference greatly appears in a system with a lower-frequency signal as the measured signal, as shown in particular from FIG. 6(A), but it does not appear so greatly in a system with a higher-frequency signal as the measured signal, as shown from FIG. 6(B). In short, the interference is increased from a side of the system with the higher-frequency signal as the measured signal toward a side of the lower-frequency signal as the measured signal. In addition, this can also be proved theoretically from graphs in the above-described FIG. 6(A), (B).

In addition, the above-described problem is not limited to the case where the noise ingredient due to the mutual interference remains, but also occurs in the case where a noise ingredient having the frequency F2 (F1) of the other system due to the other factor, such as a difference between the fluid modulation means V1 (V2) in mechanical duty, is mixed.

Accordingly, the following means are adopted to reliably reduce the errors of measurement due to the interferential noise ingredient and the like having the other frequency signal in the system with the abovedescribed one frequency signal as the measured signal.

The simplest first measure is that in the case where it is previously understood that any one (S2) of both sample fluids S1, S2 has a lower concentration or a smaller change in concentration, such as the case where it is understood that a single concentration of methane, which is one object to be measured, is clearly smaller than a total concentration of HC (THC), which is the other object to be measured (for example, in the case where a concentration of nonmethane [NMHC] in air is measured by the differential method), the sample fluid (S2) having the lower concentration (or the smaller change in concentration) is supplied to the fluid modulation means (V2) in the system of the higher modulation frequency having disadvantageous characteristics such that an interferential influence upon the other measuring system is large while the other sample fluid (S1) having the higher concentration (or the higher change in concentration) is supplied to the fluid modulation means (V1) in the system of the lower modulation frequency having advantageous characteristics such that an interferential influence upon the other measuring system is not so large. Thus, the errors in measurement due to the interferential noise ingredient of the other frequency signal in the system with one frequency signal as the measured signal can be remarkably reduced without requiring any practically difficult modification, for example, setting both fluid modulation frequencies at sufficiently large and different values or having high-grade band-pass filters with sharp frequency-cutting characteristics used as both band-pass filters in the signal treatment means.

In addition, in this case, it is desirable that the flow rate of the sample fluid S2 having the lower concentration is adapted to be larger than that of the sample fluid S1 having the higher concentration. Thus, the so-called tailing phenomenon due to the desorption of the sample fluid S1 having the higher concentration onto the sensor D and the like can be reduced in the measurement of the sample fluid S2 having the lower concentration succeeding to the measurement of the sample fluid S1 having the higher concentration.

The second measure is that in particular both fluid modulation means V1, V2 are set so that the ratio of the fluid modulation frequencies F1, F2 by them may be even numbers or reciprocals thereof (for example, F1 may be 1Hz and F2 may be 2 h 1Hz or vice versa, wherein h is an integer. Accordingly, the above-described errors of measurement due to the noise ingredient of the other frequency signal in the system with one frequency signal as the measured signal can be reliably and easily reduced without using any practically difficult measures, for example, setting both fluid modulation frequencies at great and different values or using high-grade band-pass filters having sharp frequency-cutting characteristics as both band-pass filters in the signal treatment means.

Figure 7B:
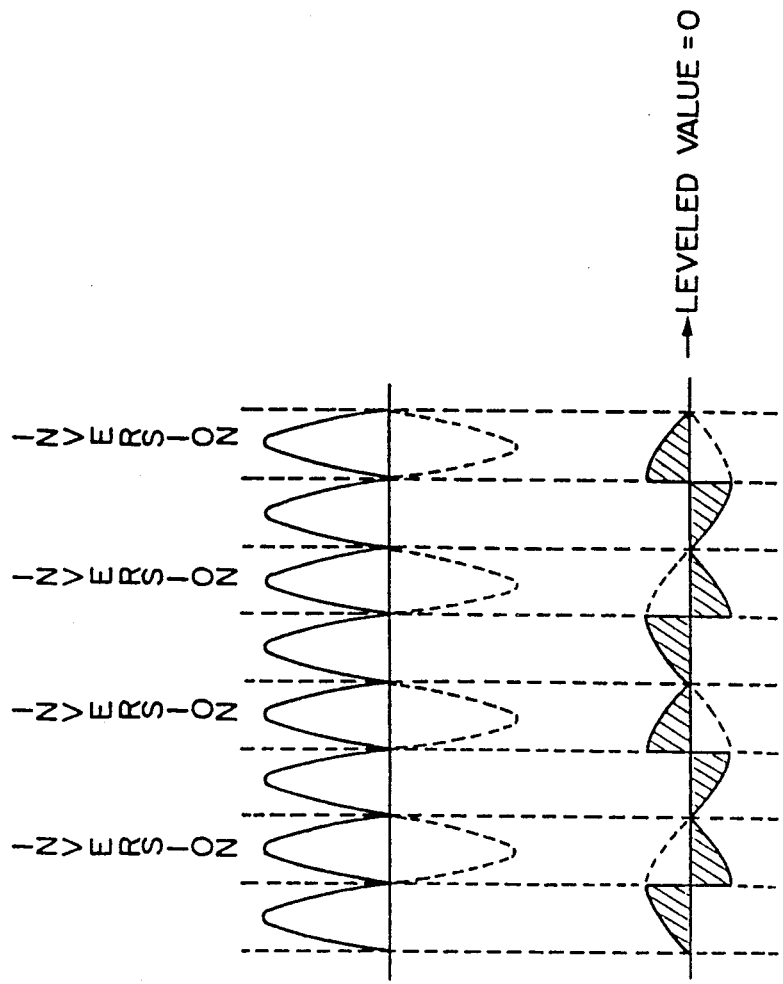

In the case where, for example, one (lower) fluid modulation frequency F1 is 1 Hz and the other (higher) fluid modulation frequency F2 is 2 Hz (which is an even number times [2 times] that of the former), even though the interferential noise ingredient having the higher fluid modulation frequency (2 Hz) is mixed in the signal, which passed through the band-pass filter a1 in the system with the lower frequency signal (1 Hz) in addition to the original signal O1 (1 Hz), as shown in FIG. 7(A), if the signal is subjected to the synchronous detection-rectification by the synchronous detector-rectifier b1, the noise ingredient (2 Hz) is subjected to the synchronous detection-rectification so that the levelled value by the subsequent leveller element c1 may be subjected to plus/minus compensation to be turned into 0, whereby the correct measured signal corresponding only to the original signal O1 (1 Hz) can be obtained from the leveller element c1. In addition, also in the system with the higher frequency signal (2 Hz) as the measured signal, contrary to the above-described case, the levelled value of the interferential noise ingredient of the lower frequency signal (1 Hz) is similarly subjected to the plus/minus compensation to be turned into 0, whereby the correct measured signal showing no error of measurement can be obtained, as understood from FIG. 7(B).

Figure 7C:
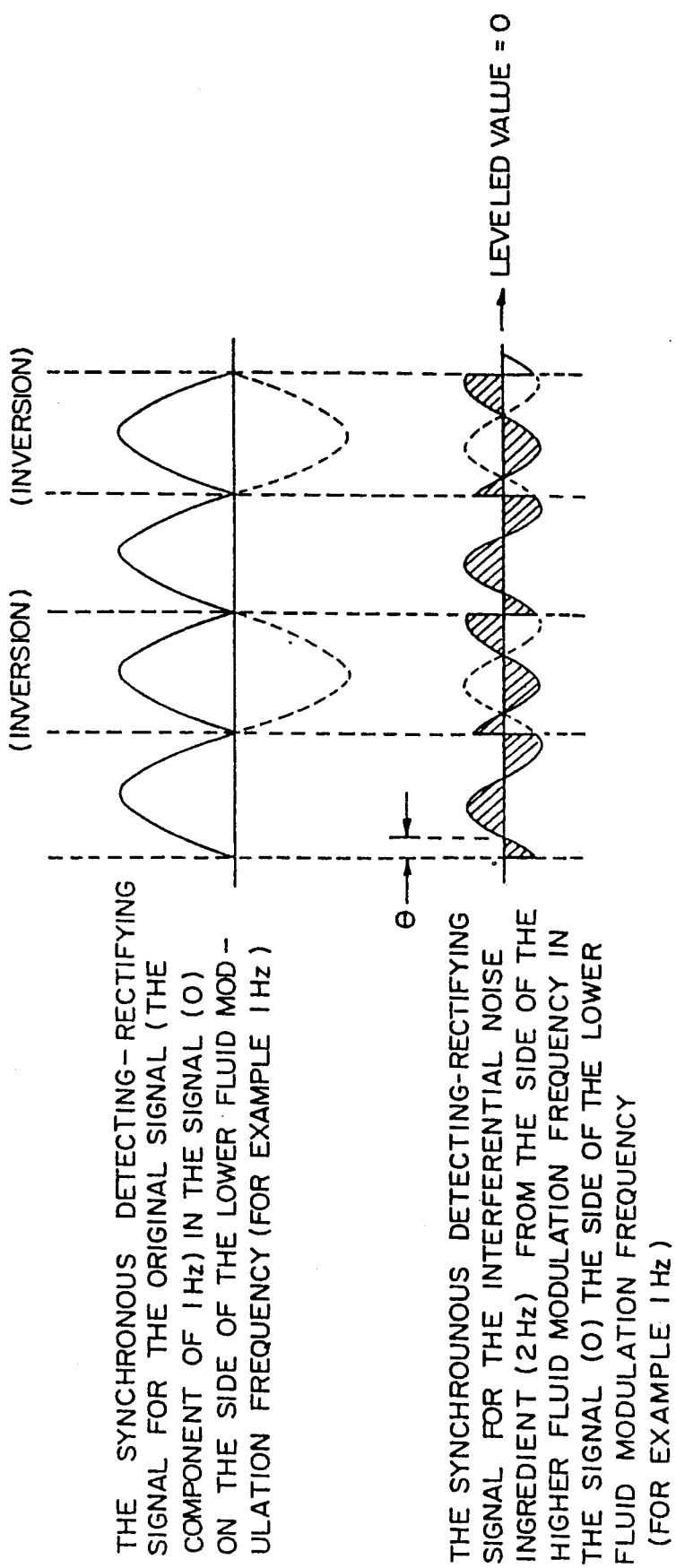
Figure 7D:
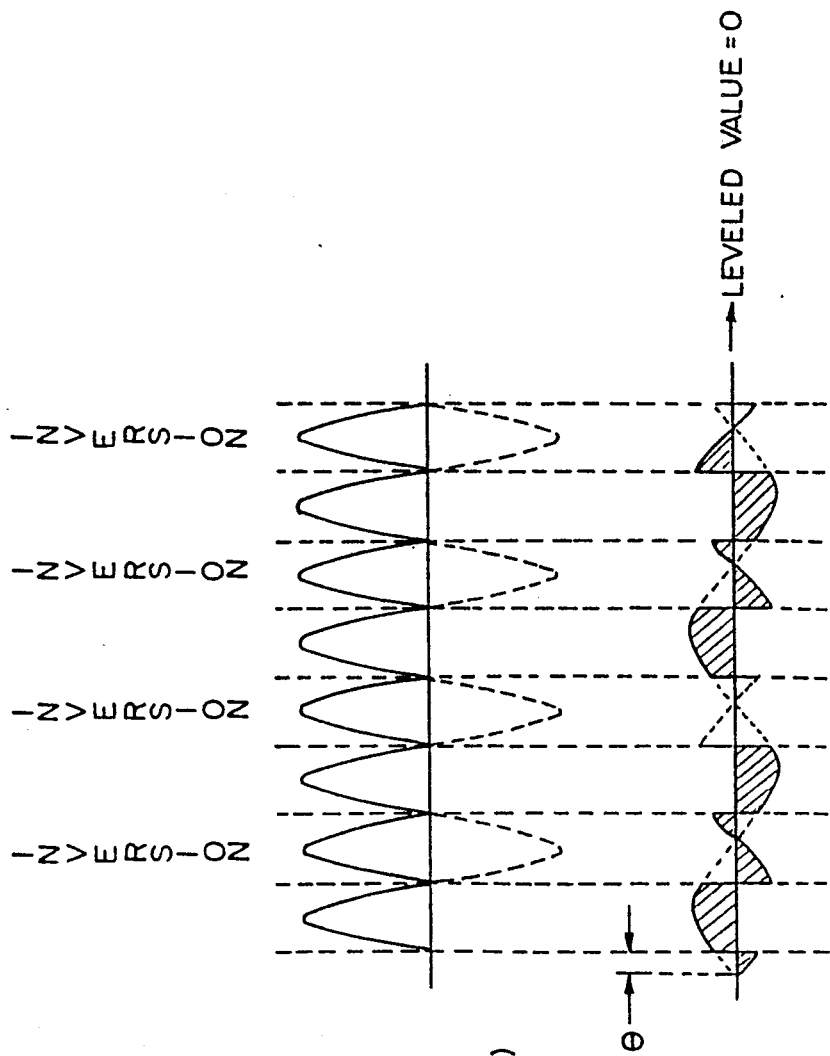

In addition, FIGS. 7(A), (B) show the case where the original signal and the interferential noise ingredient having frequencies different from each other have the same phase, but also in the case where they are different in phase by $\theta$, the levelled value of the interferential noise ingredient is subjected to the plus/minus compensation to amount to 0 likewise, as shown in FIG. 7(C), (D).

However, although the object of "reducing errors of measurement due to the interferential noise ingredient having the other frequency (F2) in the system with one frequency signal F1 as the measured signal" can be achieved by the first and second measures, the following problems still remain.

As described above, whatever constructions the fluid modulation means V1, V2 have, it is inevitable that the actual modulation frequencies of the sample fluids S1, S2 subjected to the fluid modulation by the respective fluid modulation means V1, V2 contain the noise ingredients having the frequencies other than the original fluid modulation frequencies F1, F2 due to the difference in mechanical duty resulting from errors in the manufacture, uneven driving of driving mechanism and the like, the difference in passage until the detecting portion A, and the like. In short, the noise ingredients having the frequency F2 of the other system and other high frequencies are contained in the fluid modulation frequency of the sample fluid S1 by one fluid modulation means V1 in addition to the original fluid modulation frequency F1. Similarly, the noise ingredients having the frequency F1 of the other system and other high frequencies are contained in the fluid modulation frequency of the sample fluid S2 by the other fluid modulation means V2 in addition to the original fluid modulation frequency F2.

Of these noise ingredients, the noise ingredients having high frequencies are removed by the effective operation of the band-pass filter a1 (a2) and the leveller element c1 (c2) in the signal treatment means. But the noise ingredient having the same frequency as the fluid modulation frequency F2 (F1) of the other fluid modulation means V1 (V2) generating from the fluid modulation means V1 (V2) in the system having one fluid modulation frequency F1 (F2) is mainly due to the mechanical factors, as seen in FIG. 8(A), (B) showing the case where, for example, one fluid modulation frequency F1 is set at 1 Hz, while the other fluid modulation frequency F2 is set at 2 Hz, and there is usually a difference from the original signal in phase of $\theta$ (its value has been unknown), so that it cannot be effectively removed even by the synchronous detecting operation of the synchronous detection-rectification means b1, b2. Accordingly, its levelled value does not amount to 0, whereby the errors of measurement remain.

Accordingly, the following third measure is adopted to provide an apparatus for analyzing a fluid by multi-fluid modulation mode provided with a mechanism capable of easily and reliably correcting errors of measurement due to the above-described causes, that is, "errors of measurement due to the interferential noise ingredient having the same one frequency signal from the other system in the system with one frequency signal as the measured signal."

The errors of measurement due to the interferential noise ingredient of the same one frequency signal from the other system in the system, with one frequency signal as the measured signal, are corrected by forming both fluid modulation means V1, V2 with a rotary valve provided with the passage-changing over rotor, which can be rotated and driven at the appointed period within the housing. The housing is provided with inlet ports of the sample fluids S1, S2, an inlet port of the reference fluid, an outlet port to the analyzing portion, and a discharge port. The relative phase relation between the fluid modulating operations of the rotary valves is regulated by regulating and setting the initial relative positional relation between the housing and the rotor in at least one of the rotary valves.

Figure 9A:
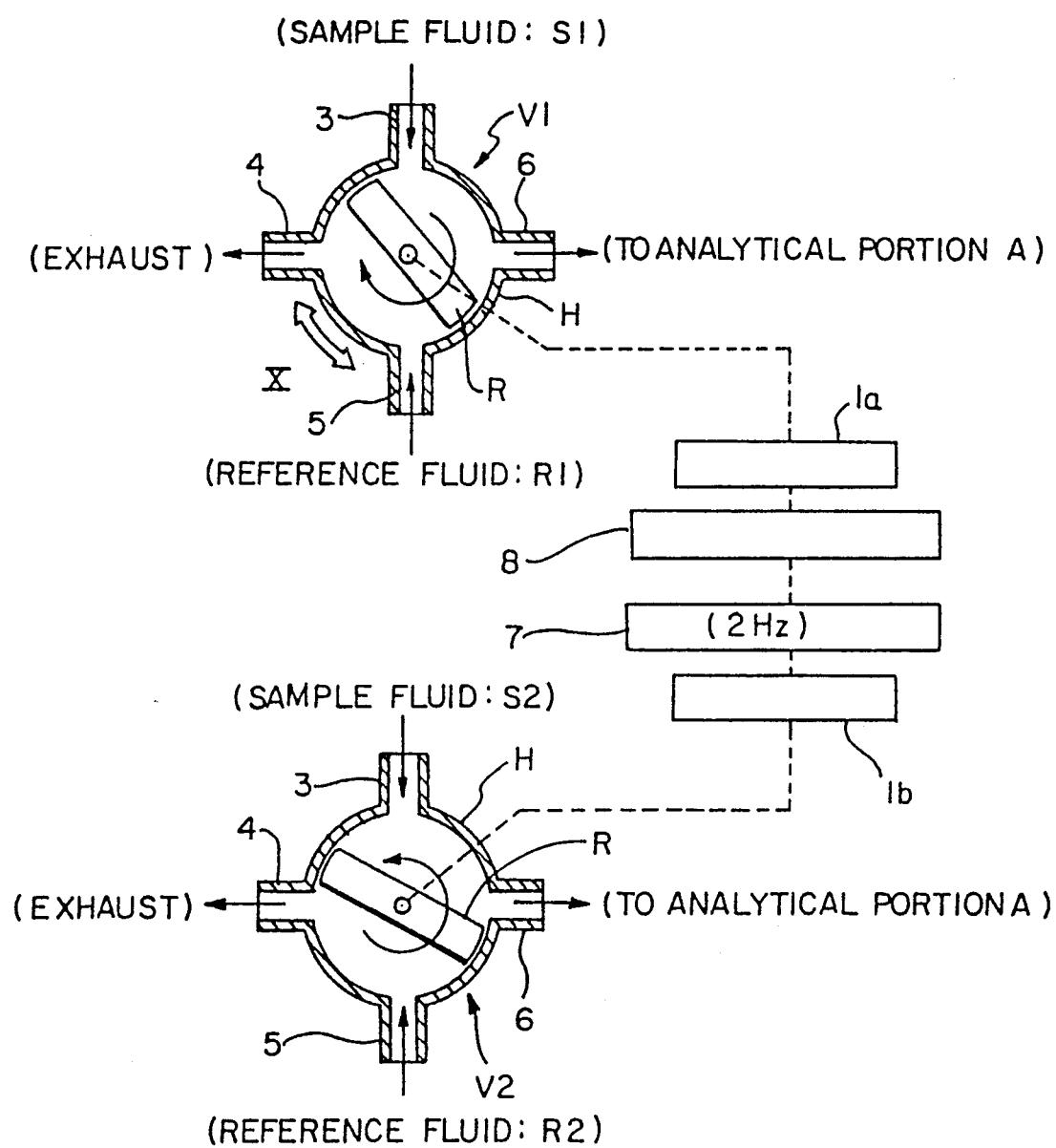
Figure 9B:
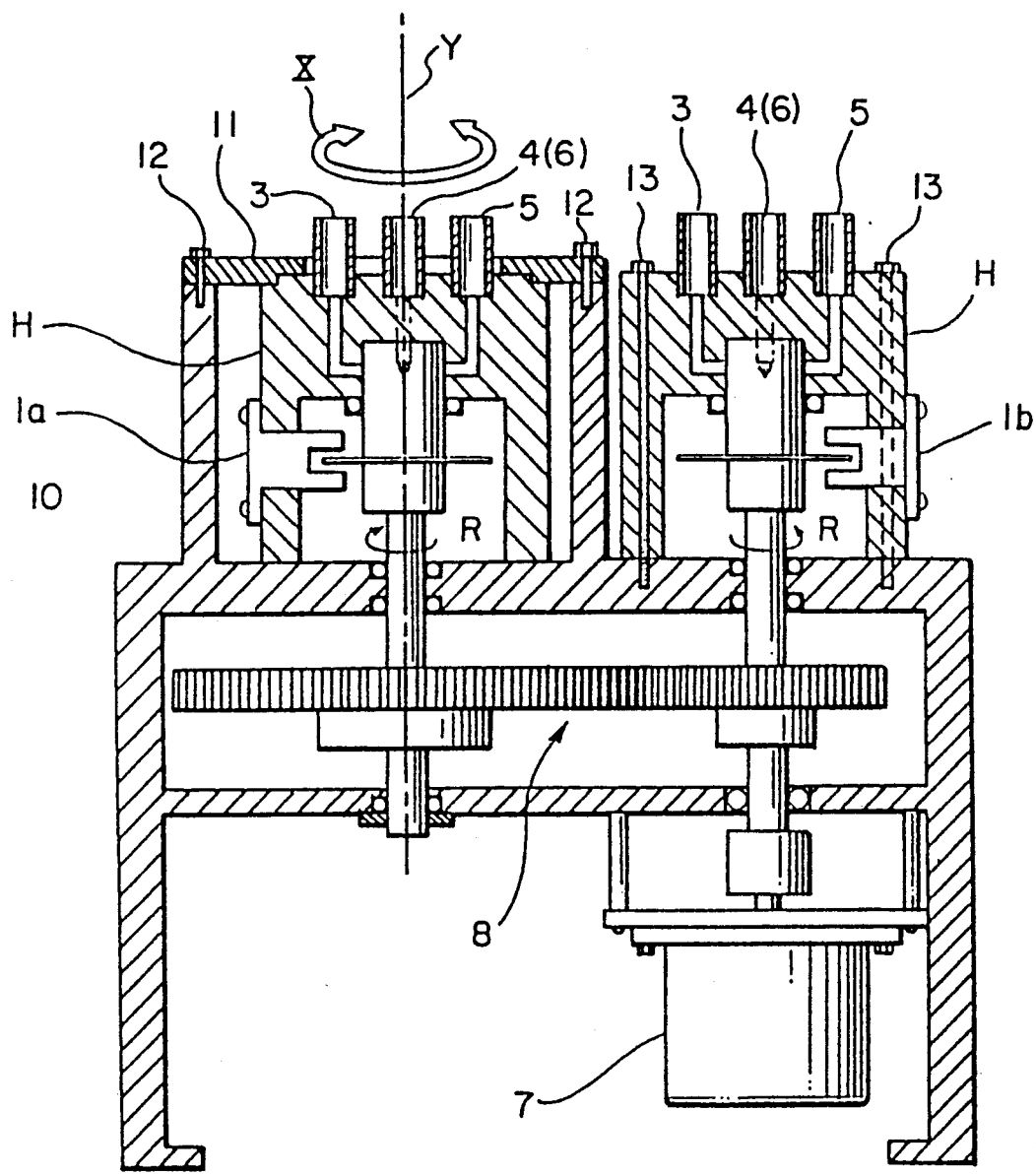

A specific construction is indicated in FIG. 9(A), (B). The respective fluid modulation means V1 (V2) are composed of a rotary valve provided with the passage-change over rotor R capable of being rotated and driven at the appointed period by means of the driving mechanism, which will be mentioned later, and disposed in the housing H which is provided with the inlet 3 of the sample fluid S1 (S2), the inlet 5 of the reference fluid R1 (R2), the outlet 6 to the analytical portion A and the exhaust port 4 to the exhaust passage.

Both rotary valves are set so that the ratio of the fluid modulation frequencies F1, F2 by them may be even numbers or reciprocals thereof, as described above (for example, F1=1 Hz and F2=2 Hz).

As described later in more detail, in at least one (in this preferred embodiment, V1) of the fluid modulation means (rotary valves) V1, V2, the housing H is adapted to be shifted or fixed, i.e., to be rotated or fixed around the axis of rotation Y of the rotor R corresponding thereto, as shown by an arrow X in the drawing, so that the initial relative positional relation between the housing H and the rotor R may be optionally regulated.

The housing H of the one fluid modulation means (rotary valve) V1 is adapted to be fixedly pressed against a base plate 10 in an optional rotary posture by means of a counter plate 11 fixedly mounted on the base plate 10 by means of bolts 12 under the condition that it is slidably and rotatably placed on the base plate 10 under a free condition. Accordingly, if the housing H is made free by loosening the bolts 12 or removing them together with the counter plate 11, the rotary position of the housing H can be easily and optionally regulated and set. On the contrary, the housing H of the other fluid modulation means (rotary valves) V2 is adapted to be directly fixedly mounted on the base plate 10 in an appointed posture.

The driving mechanism for the rotary valves R, R of the rotary valves is as follows:

According to the present preferred embodiment, the rotor R of the rotary valve composing the fluid modulation means V2 having the higher fluid modulation frequency (2 Hz) is directly rotated and driven by a motor 7, whose rotational frequency is controlled at 2 Hz. Concurrently, the rotor R of the rotary valve composing the fluid modulation means V1 having the lower fluid modulation frequency (1 Hz) is rotated and driven by a reduction gear mechanism 8 for reducing the rotational frequency of the motor 7 to one-half. An axis of rotation system from the motor 7 to the rotor R corresponding to the motor 7 and an axis of rotation system from the reduction gear mechanism 8 to the rotor R corresponding to the reduction gear mechanism 8 are provided with a synchronous signal generator 1a, 1b, such as an optical synchronous signal generator (for example, photointerrupter and the like). The generator is for forming and supplying a frequency signal expressing an actual modulating action by the respective fluid modulation means V1, V2 for the synchronous detector-rectifier b1, b2 in the signal treatment means B.

As described above, both fluid modulation means V1, V2 are composed of a rotary valve provided with the passage-change over rotor R capable of being rotated and driven at an appointed period and disposed in the housing H which is provided with the inlet 3 of the sample fluid, the inlet 5 of the reference fluid, the outlet 6 to the analytical portion and the exhaust port 4. In at least one of the rotary valves the housing is adapted to be able to be rotated or fixed around the axis of rotation of the rotor R so that the relative phase relation between the fluid modulation operations by both rotary valves can be optionally regulated by optionally regulating the initial relative positional relation between the housing H and the rotor R. Specifically, "the errors of measurement due to the interferential noise ingredient having the same one frequency signal from the other system in the system, with one frequency signal as the measured signal," can be reliably corrected by merely the remarkably easy operation of rotating the housing H of the rotary valve in one system to regulate the initial relative positional relation between the housing H and the rotor R corresponding thereto while watching the indicator so that the errors of measurement may amount to almost 0, even though errors of measurement due to the unknown difference in phase, as shown in FIG. 8(A) or (B) by the lower graph therein, are brought about in the measured value in the other system under the condition that, for example, the span fluid flows through only one measurement system as the sample fluid.

Figure 10B:
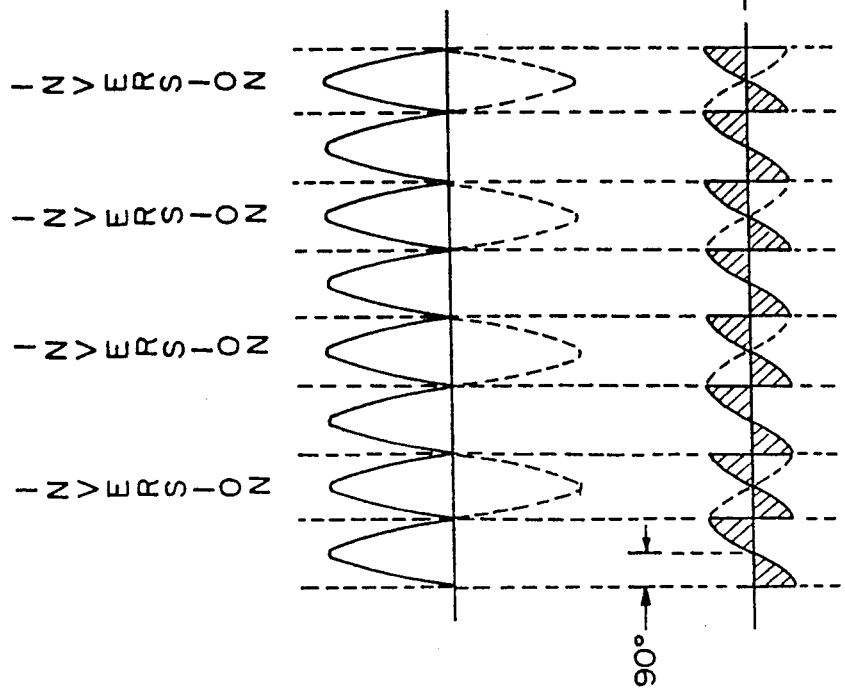

In short, the interferential noise ingredient having the same one frequency signal is corrected so that the difference from the original signal in phase may be into 90 degrees ($\pi/4$) from the optional value $\theta$, as shown in FIG. 10(A) or (B), whereby being subjected to the synchronous detection-rectification, as shown in the drawing, turns the levelled value into 0.

In addition, although the housing H is adapted to be able to be rotated or fixed relative to the rotor R merely for the rotary valve composing one fluid modulation means V1, as shown in the above-described preferred embodiment, the rotary valve composing the other fluid modulation means V2 may have such construction. In addition, both rotary valves composing the fluid modulation means V1, V2 may have such construction.

In addition, although both rotors R, R of the fluid modulation means (rotary valves) V1, V2 are driven by one motor 7 by using the reduction gear mechanism 8, as shown in the above-described preferred embodiment, both rotors R, R may alternatively be individually driven by separate motors having rotation frequencies different from each other.

FIG. 11 relates to a second basic preferred embodiment and shows a system of principal parts in the apparatus for analyzing a fluid by a multi-fluid modulation mode according to the present invention where the concentration of $CO_x$ and the like contained in, for example, the atmosphere and the sample fluids such as exhaust fluids from plants.

In this case, the analytical portion A of the apparatus generally comprises a nondispersive type infrared analyzer (NDIR), so that detectors, through which the sample fluid passes directly, do not do so such as pneumatic type detectors by condenser microphone mode, microflow mode or the like, thermopiles or solid detectors such as semiconductors, are used for the sensor D. As shown in FIG. 11, in the case where the analytical portion A comprises a so-called single-cell type NDIR, in which only one cell 1 is used, both sample fluids S1, S2, which have been subjected to the fluid modulation, are supplied to the cell 1 under a mixed condition in the same manner as in the above-described first preferred embodiment, and the absorptivity of infrared rays to be measured passing through the cell 1 is measured by the sensor D.

In addition, since other constructions and the like are the same as in the above-described first basic preferred embodiment, members having the same functions as in the first preferred embodiment are marked with the same reference numerals and marks as in the first preferred embodiment to omit the repetitive description thereof.

FIG. 12 relates to a third basic preferred embodiment and shows a system of principal parts in the apparatus for analyzing a fluid by a multi-fluid modulation mode according to the present invention where the concentration of $CO_x$ and the like is determined.

In this case, the analytical portion A comprises a so-called double-cell type nondispersive infrared analyzer (NDIR) provided with two cells 1A, 1B, so that both sample fluids S1, S2, which have been subjected to the fluid modulation, are not mixed with each other but supplied within the respective cells 1A, 1B. However, the absorptivity of the respective infrared rays to be measured passing through both cells 1A, 1B is simultaneously measured by one sensor D. In addition, one of the two cells 1A, 1B is provided with a solid filter (not shown) for use in the measurement of CO, while the other of the two cells 1A, 1B is provided with a solid filter (not shown) for use in the measurement of $CO_2$.

In addition, since other constructions and the like are the same as in the first basic preferred embodiment and the second basic preferred embodiment, members having the same functions as those in the first and second preferred embodiments are marked with the same reference numerals and marks as in the first and second preferred embodiments to omit the repetitive description thereof.

The plurality of sample fluids S1, S2 may be originally different as in the case where they are individually fed from a plurality of exhaust passages, or the single sample fluid S0 may be divided into a plurality of systems, as shown in FIG. 13. In general, the latter is used where CO and $CO_2$, NO and $NO_2$, or methane and HC other than methane (NMHC) in the one sample fluid are simultaneously and continuously measured and the like. But, in this case, usually at least one system is provided with a converter C for converting $NO_2$ to NO or converting CO to $CO_2$, a nonmethane HC remover, or a necessary filter and the like. In addition, as shown by dotted line in FIG. 13, a common RO (for example, zero gas) may also be used for the reference fluids R1, R2.

The applied preferred embodiments according to the present invention are described below.

FIG. 14 shows an apparatus for analyzing a fluid for use in the simultaneous and continuous measurement of 3 HC ingredients by a different method and multi-fluid modulation mode constructed as a first applied preferred embodiment corresponding to the first basic preferred embodiment. This is used in the case where HC ingredients contained in a sample fluid S, such as air, exhaust gas from cars and exhaust gas from plants, nonmethane HC (the second ingredient), which is a particularly noxious ingredient, is analyzed for concentration. To this end, the single concentration of methane ($CH_4$), which is the first ingredient, and the concentration (the total concentration of HC) of the third ingredient, which is defined as the sum of the first ingredient and the second ingredient, are directly measured and the single concentration of nonmethane HC, which is the second ingredient, is indirectly measured from the difference between both measured results of concentration.

The sample fluid S is divided into the first sample fluid S1 and the second sample fluid S2. The passage of the second sample fluid S2 is selected as a line for measuring the single concentration of methane ($CH_4$), which is the first ingredient, by providing a buffer tank C1 composed of a catalyzer apparatus having multiple functions. It functions as the buffer for reducing the transition response interferential influence upon the measuring system of the first sample fluid S1 when the concentration of the second sample fluid S2 is suddenly changed. It also functions as the converter for burning and removing nonmethane HC, which is the second ingredient of the second sample fluid S2 and the like, while the passage of the first sample fluid S1 is selected as a line for measuring the concentration of the third ingredient (the total concentration of HC) by providing the buffer tank C0 having only the function as the buffer for reducing the transition response interferential influence upon the measuring system of the other second sample fluid S2 when the concentration of the first sample fluid S1 is suddenly changed.

Both the second sample fluid S2 converted by the buffer tank C1 having the function as a converter (i.e., nonmethane HC is removed and only methane is contained as HC) and the first sample fluid S1 being unconverted (i.e., the same as the initial sample fluid S containing both nonmethane HC and methane) are subjected to fluid modulation at different frequencies F1, F2 (hertz) (in this preferred embodiment F1=1 Hz, F2=2 Hz) by the use of the fluid modulation means V1, V2 and the reference fluids R1, R2.

In short, the sample fluid and the reference fluid are alternately passed at the appointed frequency, and then the respective sample fluids S1, S2, which were subjected to the fluid modulation, are simultaneously and continuously supplied to the analytical portion A having only one HC sensor D.

In addition, in this case, a sensor, through which the sample fluid directly passes, such as a flame ion detector (FID), is used as the HC sensor in the analytical portion A, so that both sample fluids S1, S2 (R1, R2), which have been subjected to the fluid modulation, are supplied to the HC sensor D in the form of a mixture.

Accordingly, the signal O output from the HC sensor D through the preamplifier 2 is obtained as one measured signal (O=O1+O2) comprising individual measured signal components (O1, O2) corresponding to both sample fluids S1, S2 in the aggregate, as schematically shown.

Therefore, the signal treatment, in which the output signal O from the HC sensor D, as schematically shown in FIG. 14, has been divided into the signal components O1, O2 of the respective modulation frequencies F1, F2 for the respective sample fluids S1, S2 to rectify and level, is carried out by the use of the signal treatment means B comprising a frequency-dividing means E, a signal-rectifying means F and a subtracter G in combination. Thereby, not only the analyzed values about the respective sample fluids S1, S2 (namely, the measured results of the single concentration of the third component [total HC] and the concentration of the first component [methane]) can be individually and directly obtained, but also the single concentration of the second component (nonmethane HC) can be indirectly measured from a difference between both measured results of concentration.

In addition, the specific circuit construction of the signal treatment means B is shown in FIG. 15, which is a block circuit diagram. A subtracter g as the subtracting means G has a +input which is an output signal from the leveller element c1 in the signal treatment system about the first sample fluid S1, and has a —input which is an output signal from the leveller element c2 in the signal treatment system about the second sample fluid S2, all of which are provided in addition to the circuit shown in FIG. 4. Accordingly, the measured result of the concentration of total HC as the third component is output from the leveller element c1, the measured result of the single concentration of methane as the first component being output from the leveller element c2, and the measured result of the single concentration of nonmethane HC as the second component being output from the subtracter g.

The apparatus for analyzing a fluid for use in the simultaneous and continuous measurement of three HC components according to the above-described first applied preferred embodiment adopts the construction that the converter C1 for removing nonmethane HC from the original sample fluid S is provided. But this converter C1 has exhibited fundamental functional defects in that methane, which is not to be removed, is also removed in a quantity of about 5 to 10% under the condition that nonmethane HC can be completely burned and removed, while nonmethane HC cannot be completely removed under the condition that methane can remain. Furthermore, the catalytic efficiency thereof is changed over time. Accordingly, the errors of measurement due to the above-described fundamental functional defects have been inevitable. In addition, the concentration of nonmethane HC, which is the most important object component to be measured, cannot be directly measured, but can be only indirectly obtained as the difference between the concentration of total HC and the concentration of methane, so that there is the possibility that the errors are brought about also in the subtraction of the measured results of both concentrations.

The apparatus for analyzing a fluid for use in the simultaneous and continuous measurement of three HC components according to the second applied preferred embodiment shown in FIGS. 16, 17 is devised so as to eliminate the above-described problems in the apparatus according to the first applied preferred embodiment.

As shown in FIG. 16, Which is a general block diagram, the sample fluid S, such as air, exhaust gas from cars and exhaust gas from plants, is divided into two passages, one of the two passages being provided with a buffer tank (dummy) C0 to flow the original sample fluid S therethrough as a nonconverted sample fluid S0. The other passage is provided with the converter C1 comprising the catalytic apparatus for completely burning and removing nonmethane HC of HC components contained in the sample fluid S and the like to flow a converted sample fluid S1 toward the downstream side of the converter C1.

The unconverted sample fluid S0 (i.e., the original sample fluid S containing both nonmethane HC and methane) and the converted sample fluid S1 converted by the converter C1 (i.e., from which nonmethane HC was removed, and containing merely methane as HC) was subjected to the fluid modulation by the use of the suitable fluid modulation means V1, V2, respectively, with the converted sample fluid S1 and the zero fluid R0 as the reference fluid, respectively, at the different frequencies F1, F2 (hertz) (in this preferred embodiment F1=1 Hz, F2=2 Hz) (i.e., the sample fluid and the reference fluid were alternately passed at the appointed frequency), and then the respective sample fluids S1 (and R0), S0 (and S1), which were subjected to the fluid modulation, are simultaneously and continuously supplied to the analytical portion A provided with only one HC sensor D. In addition, in this case, a sensor, through which the sample fluid directly passes, such as a flame ion detector (FID), is used as the HC sensor in the analytical portion A, so that both sample fluids S1, S0, which have been subjected to the fluid modulation, are supplied to the HC sensor D in the form of a mixture.

Accordingly, the signal 0 output from the HC sensor D through the amplifier 2 is obtained as one measured signal (0=01+02) comprising individual measured signal components 01 (the concentration of total HC based on the concentration of methane, in short, the signal about nonmethane HC), 02 (the signal about the concentration of methane) corresponding to both sample fluids S1, S0 in sum, as schematically shown.

Therefore, the signal treatment, in which the output signal 0 from the HC sensor D, as schematically shown in FIG. 16, is divided into the signal components 01, 02 of the respective modulation frequencies F1, F2 for the respective sample fluids S1, S0 to rectify and level, is carried out by the use of the frequency-dividing means E and the signal-rectifying and levelling means F in the signal treatment means B so that not only the analyzed values about the respective sample fluids S1, S0 (in short, the fundamental measured results of the concentration of nonmethane HC and the single concentration of methane) can be individually and directly obtained, but also the fundamental measured results of both nonmethane HC and methane are corrected by correcting means H, which will be mentioned later in detail, respectively, to compensate for the errors of measurement due to the fundamental defects of the converter C. Also, the concentration of total HC can be indirectly measured by means of an adding means I for adding both corrected measured results of the concentration of both nonmethane HC and methane.

A specific circuit construction of the signal treatment means B is shown in FIG. 17, which is a block circuit diagram. A correcting circuit h as the correcting means F for calculating the correct concentrations of nonmethane HC and methane by a method, which will be mentioned later, on the basis of the fundamental concentration signals of nonmethane HC and methane obtained by both leveller elements c1, c2 is provided in the lower reaches of both leveller elements c1, c2. Furthermore, the correct concentration of total HC can be output by an adding circuit i as the adding means I for calculating a sum of the correct concentrations of nonmethane HC and methane output from the correcting circuit h.

The correction for the fundamental concentration signals of nonmethane HC and methane by the correcting circuit h is carried out as follows:

Provided that a true concentration of methane contained in the sample fluid S is p, a true concentration of nonmethane HC being q, and an oxidation (combustion) coefficient K of methane in the converter C1, of which oxidation (combustion) coefficient of nonmethane HC is set at 100%, a fundamental measured concentration p' of methane output from the leveller element c2 in the signal treatment means B and a fundamental measured concentration q' of nonmethane HC output from the leveller element c1 is expressed by the following equation (1), (2), respectively.

$$p' = X(1-K)p \quad (1)$$

$$q' = Y[(p + q) - (1 - k)p] \quad (2)$$
$$= Y(Kp + q)$$

(wherein X, Y are coefficients determined depending upon the measured apparatus.)

Accordingly, if three unknown coefficients K, X, Y in these two equations become clear, the true concentrations of methane and nonmethane HC p, q can be obtained by the operation on the basis of the fundamental measured results thereof p', q'.

For example, in the compensation of the apparatus,
(1) Since p=0 and q is known, the equation $$q' = Yq$$

results from equation (2) by carrying out the measurement using propane ($C_3H_8$), one of which is one kind of nonmethane HC, of the known concentration as the compensation gas, so that the coefficient Y is calculated from q' (the fundamental measured concentration output from the leveller element c1)/the true concentration (known).

(2) Subsequently, $$p_1' = X(1-K)p_1$$

$$p_2' = X(1-K)p_2$$

results from the equation (1) by carrying out the measurements in turn using a mixture gas comprising methane ($CH_4$) and pure air having two kinds of known concentration $p_1$, $p_2$ as the compensation gas, so that the other two coefficients X, Y can be calculated from the above-described equations on the basis of $p_1'$, $p_2'$ (the fundamental measured concentrations output from the leveller element c2) and the known true concentrations $p_1$, $p_2$.

Accordingly, if three coefficients, which were obtained in the above-described manner when compensated, are set in the correcting circuit h, the correcting circuit h can operate and output the correct values of the concentrations of nonmethane HC and methane from equations (1), (2) on the basis of the fundamental measured concentrations q', p' of nonmethane HC and methane output from both leveller elements c1, c2 also in the measurement.

As described above, in the apparatus according to this second applied preferred embodiment, the unconverted sample fluid S0 in one passage is subjected to the fluid modulation at the frequency F1 with the converted sample fluid S1 as the reference fluid (i.e., the concentration of methane contained in the converted sample fluid S1 is the standard), while the converted sample fluid S1 obtained by removing nonmethane HC in the sample fluid S by means of the converter C1 in the other passage is subjected to the fluid modulation at the frequency F2 with the zero fluid R0 as the reference fluid. Furthermore, in the signal treatment means B, not only is the output signal 0 from only one HC sensor D at first divided into respective signal components 01, 02 of the respective modulation frequencies F1, F2 by the use of the suitable frequency-dividing means E and the signal-rectifying and levelling means F to rectify and level, whereby the concentration of methane and the concentration of nonmethane HC can be individually and directly obtained, but also the measured result of the concentration of nonmethane can be corrected by means of the suitable correcting means H utilizing the measured result of the concentration of methane. Thereby, the errors of measurement due to the fundamental functional defects of the converter C1 for use in the removal of nonmethane HC can be effectively compensated.

Also, as described above, the concentration of nonmethane HC, which is the most important object component to be measured, can be directly measured, so that it is not always necessary to measure the concentration of total HC as in conventional apparatuses and the apparatus according to the preceding application. Accordingly, obtaining a difference between the concentration of total HC and the concentration of methane becomes unnecessary, whereby not only is the signal treatment means simplified, but also the possibility of errors accompanied by subtraction is eliminated.

FIGS. 18, 19 show an apparatus for analyzing a fluid for use in the simultaneous and continuous measurement of three $NO_x$ components using the differential method and the multi-fluid modulation mode according to the third applied preferred embodiment corresponding to the first basic preferred embodiment. Also, this apparatus is used in the case where the concentration of $NO_2$ (the second component), which is particularly noxious of $NO_x$ components contained in the sample fluid S, such as air, exhaust gas from cars and exhaust gas from plants, is analyzed. To this end, the single concentration of NO, which is the first component, and the concentration of the third component (total concentration of NO), which is defined as the sum of both the first component and the second component, are directly measured and the single concentration of $NO_2$, which is the second component, is indirectly measured from the difference between the measured results of both concentrations.

In the apparatus according to this preferred embodiment, as obvious from FIG. 18, which is a general block diagram, the catalytic apparatus and the like for carrying out the treatment of converting (reducing) $NO_2$, which is the second component, into NO, which is the first component, are used as the converter C2 to be provided in the passage of the first sample fluid S1 and the NO sensor, such as chemical luminescence detector (CLD), is used as the sensor D in the analytical portion A.

Accordingly, in this case, the passage of the first sample fluid S1 provided with the converter C2 therein becomes the line for measuring the concentration of the third component (total concentration of NO) in the first sample fluid S1. The passage of the second sample fluid S2 provided with the buffer tank (dummy) C0 therein becomes the line for measuring the single concentration of NO, which is the first component. As a result, as shown in FIG. 19, which is a block circuit diagram showing the signal treatment means B, the measured result of the concentration of the third component (total concentration of NO) is output from the leveller element c1 in the system of the first sample fluid S1. The measured result of the single concentration of NO, which is the first component, is output from the leveller element c2 in the system of the first sample fluid S1. The measured result of the single concentration of $NO_2$, which is the second component, is output from the subtracter g' as the subtracting means G'.

In the apparatus according to the above-described first to third applied preferred embodiments, the converter C2 (C1), which functions as the buffer tank, is provided in the supply passage of the sample fluid SI (S2) to one fluid modulation means V1 (V2) and the buffer tank C0 as the dummy is provided in the supply passage of the sample fluid S2 (S1) to the other fluid modulation means V2 (V1). The reason for this is described below.

Since the above-described factors for errors of measurement, such as the incomplete cutting-off characteristics of the band-pass filters a1, a2 and the difference between the fluid modulation means V1, V2 in mechanical duty, have a characteristic of being brought about at all times, the average value can be turned into almost 0 within the usual measuring time (sufficiently long) by using the above-described measure that "both fluid modulation means V1, V2 are set so that the ratio of the fluid modulation frequencies F1, F2 by them may be even numbers or reciprocals thereof." But in the case where the concentration of the sample fluid S1 is suddenly changed (for example, in a stepped manner), for example, where in the zero-span calibration prior to the measurement in order to carry out the initial regulation of one measuring system (in this drawing the side having the fluid modulation frequency of 1 Hz), the condition in which the zero fluid is passed through that measuring system as the sample fluid S1 is changed over to the condition in which the span fluid is passed through that measuring system as the sample fluid S1, as shown in FIG. 20, so-called beard-like noises x, x corresponding to the sudden change of the sample fluid S1 in concentration are produced in the output signal from the other measuring system (the side having the fluid modulation frequency of 2 Hz) as the transition response interferential influence, when the converter C1 (C2) and buffer tank C0 do not exist. According to the result by the simulation, it has been understood that the errors of measurement due to the production of such beard-like noises x, x amount to several percent. This phenomenon is not shown, but similarly appears in an output signal from one measuring system (the side of 1 Hz) also in the case where the initial regulation of the other measuring system (the side of 2 Hz) is carried out. In addition, this phenomenon can be brought about in not only the zero-span calibration which was hereinbefore described, but also in the measurement.

It is for this reason that the beard-like noises x, x due to the above-described transition response interferential influence are produced that the sudden change of concentration of this type has the property of being produced at an optional timing (phase) and instantaneously. Accordingly, the errors of measurement due to the beard-like noises x, x by such transition response interferential influence cannot be cancelled in a time integration manner since the above-described factors of the errors of measurement have the property of being brought about at all times.

In view of the above-described circumstances, in the apparatus according to the respective applied preferred embodiments, a construction is adopted in which the converter C1 (C2) or the buffer tank C0 as the dummy is provided on the way of the supply passage of the sample fluid S1, S2 to both fluid modulation means V1, V2 as the buffer tank for reducing the influence of the transition response interference upon the measuring system of the other sample fluid S2, S1 when the concentration of the sample fluid S1, S2 is suddenly changed. Thus, as schematically shown in FIG. 21, even though the concentration of the sample fluid S1 (S2) introduced into one measuring system is suddenly changed (changed in a stepped manner), the sample fluid S1 (S2) is subjected to the relaxation of the sudden change in concentration in the buffer tank C1 or C2 (C0) and then supplied to the fluid modulation means V1 (V2). Accordingly, not only the original measurement of concentration in one measuring system can be carried out without hindrance, but also the influence of the transition response interference upon the other measuring system, that is, the generation of the beard-like noises x, x, can be reduced as far as possible.

FIG. 22 shows one example of a two-component measurement type infrared gas analyzer constructed as the fourth applied preferred embodiment corresponding to said third basic preferred embodiment adapted to simultaneously measure CO and $CO_2$ as the object components to be measured. Referring to FIG. 22, reference numerals 1A, 1B designate cells disposed in parallel to each other and reference numerals 13, 14 designate light sources for emitting infrared rays to the cells 1A, 1B.

Reference numeral 15(D) designates a solid sensor provided with solid filters 15a, 15b on a side facing the cells 1A, 1B of a body provided with two light paths, for example, mirror finished therein so as to correspond to the cells 1A, 1B and a solid sensor element 15c at a position, upon which a light is incident through the light path, on the other end side of the body. One solid filter 15a is constructed as a $CO_2$-measuring filter having an absorption band at almost the same wavelengths as characteristic absorption wavelengths of CO, while the other solid filter 15b is constructed as a CO-measuring filter having an absorption band at almost the same wavelengths as characteristic absorption wavelengths of $CO_2$. Reference numeral 2 designates a preamplifier disposed on an output side of the sensor 15(D).

Reference numerals V1, V2 designate fluid modulation means for simultaneously and continuously changing and supplying the sample gas S (S1, S2) and the reference gas R (R1, R2) to the cells 1A, 1B at an appointed period and are formed of, for example, a rotary valve. The modulation frequencies of the sample gas S and the reference gas R by these fluid modulation means V1, V2 are adapted to be different from each other. For example, the modulation frequency of the fluid modulation means V1 is 1 Hz, while that of the fluid modulation means V2 is 2 Hz. Accordingly, in the case where the cells 1A, 1B are supplied with the sample gas S and the reference gas R by the fluid modulation means V1, V2 having the above-described modulation frequencies, an output signal 0 comprising a signal having a band in the vicinity of the modulation frequency for the cell 1A and a signal having a band in the vicinity of the modulation frequency for the cell 1B in a lump is output from the sensor 15D.

B designates signal treatment means connected to an output side of the sensor 15D through the preamplifier 2. The specific construction of the signal treatment means B is the same as that shown in FIG. 4 and adapted to divide the output signal 0 from the sensor 15D through the preamplifier 2 into two signal treatment systems followed by treating.

Accordingly, a signal component a corresponding to the cell 1A and a signal component b corresponding to the cell 1B are output from this signal treatment means B under conditions independent of each other, whereby the signal a corresponding to the object component CO to be measured and the signal b corresponding to the object component $CO_2$ to be measured can be obtained, and thus the concentrations of two object components $CO_2$, CO can be obtained.

FIG. 23 shows a modification of the above-described fourth applied preferred embodiment. Referring to FIG. 23, reference numeral 20(D) designates a condenser microphone-type detector comprising light-receiving chambers 20a, 20b disposed so as to correspond to the cells 1A, 1B, respectively, and solid filters 21a, 21b being disposed between the cells 1A, 1B and the light-receiving chambers 20a, 20b, respectively. The solid filters 21a, 21b have the same construction as that of the solid filters 15a, 15b in the above-described fourth applied preferred embodiment. In addition, CO and $CO_2$ are enclosed within the light-receiving chamber 20a, 20b, respectively. Other constructions and operations are the same as those in the above-described fourth applied preferred embodiment.

FIG. 24 shows one example of a one-component measurement-type infrared gas analyzer constructed as the fifth applied preferred embodiment corresponding to the third basic preferred embodiment and adapted to be capable of compensating an interferential influence by components (for example, $CO_2$) other than the object component to be measured (for example, CO).

Referring to FIG. 24, reference numerals 1A, 1B designate cells disposed in parallel to each other, and reference numerals 23, 24 designate light sources for emitting infrared rays to the cells 1A, 1B, respectively. Reference numeral 25(D) designates a condenser microphone-type detector comprising light-receiving chambers 25a, 25b disposed so as to correspond to the cells 1A, 1B, respectively, and CO is enclosed within the light-receiving chambers 25a, 25b.

A filter 26 having an absorption band at almost the same wavelengths as characteristic absorption wavelengths of CO, which is an object component to be measured, is disposed in an optical path on a side of one cell 1B, but such a filter is not disposed in an optical path on a side of the other cell 1A.

V1, V2 designate fluid modulation means for simultaneously and continuously changing over and supplying the sample gas S (S1, S2) and the reference gas R (R1, R2) to the cells 1A, 1B, respectively, at an appointed period and formed of, for example, a rotary valve. Modulation frequencies of the sample gas S and the reference gas R by these fluid modulation means V1, V2 are adapted to be different from each other. For example, the modulation frequency of the fluid modulation means V1 is 1 Hz, while the modulation frequency of the fluid modulation means V2 is 2 Hz. Accordingly, in the case where the sample gas S and the reference gas R are supplied to the cells 1A, 1B by the fluid modulation means V1, V2 having the above-described modulation frequencies, an output signal 0 comprising a signal having a band in the vicinity of the modulation frequency for the cell 1A and a signal having a band in the vicinity of the modulation frequency of the cell 1B in a lump is output from a sensor 25(D).

Reference numeral 2 designates a preamplifier and reference B designates signal treatment means. Their specific constructions are the same as that shown in FIG. 4 and adapted to divide the output signal 0 from the sensor 25(D) through the preamplifier 2 into two signal treatment systems followed by treating.

Accordingly, a signal corresponding to the cell 1A on a side where the filter is not provided (a concentration signal corresponding to the object component to be measured + the interferential component: c+d) and a signal component corresponding to the cell 1B on a side where the filter 26 is provided (a concentration signal corresponding to the interferential component: d) are output from the signal treatment means B independently of each other.

The concentration signal c corresponding only to the object component CO to be measured can be obtained by calculating a difference between both signals c+d, d by means of a subtracter 20, whereby an influence by the interferential component $CO_2$ can be effectively compensated without requiring any regulating operation even though only one sensor 25(D) is used, and thus the concentration of the object component CO to be measured can be measured with high accuracy.

FIG. 25 shows one example of a differential concentration measurement-type infrared gas analyzer constructed as a sixth applied preferred embodiment corresponding to the third basic preferred embodiment adapted to be capable of measuring the differential concentration of the object component to be measured and the concentration of the object component to be measured contained in the respective sample gas S1 (S2) for two sample gases S1, S2 containing the object component to be measured (for example, $CO_2$) at comparatively high concentrations close to each other. This gas analyzer can be particularly useful in the case where an extent of $CO_2$ in air consumed by the assimilation of carbonic acid of a plant is measured.

Referring to FIG. 25, reference numerals 1A, 1B designate long and short cells disposed in parallel to each other and reference numerals 33, 34 designate light sources for emitting infrared rays to the cells 1A, 1B, respectively. Reference numeral 35(D) designates a condenser microphone-type sensor comprising light-receiving chambers 35a, 35b disposed so as to correspond to the cells 1A, 1B, respectively, and $CO_2$ is enclosed within the light-receiving chambers 35a, 35b. Reference numeral 2 designates a preamplifier disposed on an output side of the sensor 35(D).

Reference numerals V1, V2 designate fluid modulation means disposed so as to correspond to the cells 1A, 1B, respectively, and formed of, for example, a rotary valve. One fluid modulation means V1 is adapted to change over the first sample gas S1 (for example, a gas obtained from a chamber where the assimilation of carbonic acid is carried out and having a concentration e of $CO_2$) and the second sample gas S2 (air supplied to the chamber and having a concentration f of $CO_2$) simultaneously and continuously at an appointed period, for example, at a modulation frequency of 1 Hz, and supply them to the long cell 1A. The other fluid modulation means V2 is adapted to change over the second sample gas S2 and a reference gas R ($N_2$ and the like not containing $CO_2$, which is the object component to be measured) simultaneously and continuously at an appointed period, for example, at a modulation frequency of 2 Hz, and supply them to the short cell 1B.

Accordingly, in the case where the first sample gas S1 and the second sample gas S2, the second sample gas S2 and the reference gas R, are supplied to the cells 1A, 1B, respectively, by means of the fluid modulation means V1, V2 having the above-described modulation frequencies, respectively, an output signal 0 comprising a signal having a band in the vicinity of the modulation frequency for the cell 1A and a signal having a band in the vicinity of the modulation frequency for the cell 1B in the aggregate is output from the sensor 35(D).

B designates signal treatment means having the same construction as that shown in FIG. 4 and which is adapted to divide the output signal 0 from the sensor 35(D) through the preamplifier 2 into two signal treatment systems followed by treating.

Accordingly, signals expressing a difference $|e-f|$ between concentrations of the object component to be measured contained in both sample gases S1, S2 and a concentration f of the object component to be measured contained in one of said sample gases S2, respectively, can be simultaneously obtained from the said treatment means B, so that the concentration e of the object component to be measured contained in the other sample gas S1 can also be obtained on the basis of these concentration signals.

In addition, since the second sample gas S2 containing the object component to be measured at higher concentrations is adapted to be supplied to the short cell 1B, the concentration of the object component to be measured contained in the second sample gas S2 can be measured with high accuracy, whereby the concentration of the object component to be measured contained in the first sample gas S1 can also be measured with high accuracy, and thus the concentration of the object component to be measured in the two sample gases S1, S2 at comparatively higher concentrations close to each other and the difference between the above-described concentrations can be measured with high accuracy even though only one sensor 35(D) is used.

FIG. 26 shows one example of an infrared gas analyzer, which is one kind of absorption analyzer constructed as a seventh applied preferred embodiment corresponding to said third basic preferred embodiment, and adapted to be capable of continuously measuring low concentrations up through high concentrations so as to be preferably used for the measurement of a sample gas showing an increased change in concentration.

Referring to FIG. 26, reference numerals 1A, 1B designate cells having different cell lengths (hereinafter referred to as a long cell 1A and a short cell 1B) disposed in series to each other between a light source 43 for emitting infrared rays and a sensor 45(D).

The sensor 45(D) is formed of, for example, a condenser microphone-type detector. The same gas as an object component to be measured or a gas having an absorption band at almost the same wavelengths as characteristic absorption wavelengths of the object component to be measured is enclosed within the sensor 45(D).

Reference numerals V1, V2 designate fluid modulation means for simultaneously and continuously changing over and supplying a sample gas S (S1, S2) and a reference gas R (R1, R2) to the long cell 1A and the short cell 1B, respectively, at an appointed period, the modulation means being formed of, for example, a rotary valve. Modulation frequencies of the sample gas S and the reference gas R by these fluid modulation means V1, V2 are adapted to be different from each other. For example, the modulation frequency of the fluid modulation means V1 is 1 Hz, while the modulation frequency of the fluid modulation means V2 is 2 Hz. Accordingly, in the case where the sample gas S and the reference gas R is supplied to the long cell 1A and the short cell 1B, respectively, by the fluid modulation means V1, V2 having the above-described modulation frequencies, an output signal 0 comprising a signal having a band in the vicinity of the modulation frequency for the long cell 1A and a signal having a band in the vicinity of the modulation frequency for the short cell 1B in the aggregate is output from the sensor 45(D).

B designates signal treatment means connected to an output side of the sensor 45(D) through a preamplifier 2. The construction of the signal treatment means B is the same as that shown in FIG. 4 and is adapted to divide the output signal 0 from the sensor 45(D) through the preamplifier 2 into two signal treatment systems followed by treating.

With the infrared gas analyzer having the above-described construction, if the sample gas S and the reference gas R are simultaneously and continuously supplied to the long cell 1A and the short cell 1B, respectively, at the modulation frequencies of 1 Hz and 2 Hz, respectively, by the fluid modulation means V1, V2, one sensor 45(D) provided in common to the long cell 1A and the short cell 1B outputs the output signal 0 comprising a signal component corresponding to the long cell 1A (signal component corresponding to a lower concentration range [for example, about ppm to 1%]: $a_L$) and a signal component corresponding to a higher concentration range [for example, 1% or more]: $a_H$) in an aggregate. Moreover, since both signal components $a_L$, $a_H$ are modulated at different frequencies, the signal $a_L$ and the signal $a_H$ corresponding to the lower concentration range and the higher concentration range of the object component to be measured, respectively, can be obtained by dividing the output signal 0 into the signal components $a_L$, $a_H$ having the respective modulation frequencies for the long cell 1A and the short cell 1B to be rectified and levelled, respectively.

As obvious from Lambert-Beer's law, the general absorption analyzer exhibits nonlinear output characteristics as shown in FIG. 27. To the contrary, with the apparatus according to the above-described seventh applied preferred embodiment, both the concentration in the lower concentration range of the object component to be measured and that in the higher concentration range of the object component to be measured can be obtained with high accuracy.

4. Effects of the Invention

As obvious from the above detailed description, according to the present invention, at first one measured signal comprising the respective measured signal components corresponding to all sample fluids in an overlapped manner in the aggregate is obtained from only one sensor by subjecting a plurality of sample fluids to a fluid modulation by reference fluid at frequencies different from each other and supplying an analytical portion (provided with only one detector) simultaneously and continuously with the respective sample fluids which have been subjected to fluid modulation and then the signal treatment to rectify and level, in which one measured signal is divided into signal components having the respective modulation frequencies for respective sample fluids is carried out, whereby the analyzed values about the sample fluids are obtained. Thus, the simple and inexpensive analyzer provided with only one sensor can be used even in the simultaneous and continuous analysis of a plurality of ingredients contained in the one sample fluid or the simultaneous and continuous analysis of the specific ingredient contained in a plurality of different sample fluids. Accordingly, not only the measurement system can be small-sized and simplified and the cost can be reduced easily in comparison with the conventional general methods of analyzing a fluid, which have required a plurality of sensors, and the regulation of the sensor can be easily carried out in a short time, but also no error in zero calibration and no difference in sensitivity are produced among a plurality of sensors as in the conventional methods, so that a notable effect is exhibited in that an excellent accuracy of measurement can be secured. In addition, the signal treatment means comprises a plurality of signal treatment systems comprising the band-pass filter, the synchronous detector-rectifier and the leveller element connected to each other in series and in parallel, so that the apparatus can be remarkably simplified and inexpensive in comparison with other means using, for example, the computer or lock-in amplifier. Furthermore, the apparatus is adapted to be capable of making up for the frequency-dividing action, for which there is the possibility that the use of merely the band-pass filter is insufficient, by the use of the synchronous detector-rectifier, whereby carrying out the division having a high accuracy, so that a remarkably superior effect can be exhibited in that the signal treatment capacity (S/N ratio) is remarkably superior to the apparatus having such construction that the frequency is divided by the band-pass filter and then immediately the absolute value rectification is carried out can be obtained.

What is claimed is:

1. An apparatus for analyzing a fluid by a multi-fluid modulation mode comprising:
    fluid modulation means for subjecting a plurality of sample fluids to a fluid modulation by a reference fluid at frequencies different from each other;
    an analytical portion provided with only one detector, to which said respective sample fluids subjected to said fluid modulation are simultaneously and continuously supplied; and
    signal treatment means for dividing an output signal from said analytical portion into signal ingredients having respective modulation frequencies for said sample fluids to carry out a rectification and a levelling treatment, said signal treatment means comprising a plurality of band-pass filters disposed in parallel to each other for passing only signals within bands in the vicinity of said respective modulation frequencies from the output signal from said detector, a synchronous detector-rectifier disposed in the lower stream of each of said plurality of band-pass filters for detecting and rectifying an output signal from the band-pass filter synchronously with the practical fluid-modulating action by the fluid modulation means corresponding to the frequency of the passband, and a leveller element disposed in the lower reaches of said respective synchronous detector-rectifiers for levelling an output signal from said respective synchronous detector-rectifiers, whereby analytical values about said respective sample fluid are obtained.

2. The apparatus according to claim 1 wherein said fluid modulation means comprises one of a rotary value, a four-way changing-over electromagnetic value, and a three-way changing over electromagnetic value.

3. The apparatus according to claim 1 wherein said frequencies are one of even numbers and reciprocals of even numbers.

4. A fluid analyzer for use in a simultaneous and continuous measurement of three ingredients, including a first ingredient and a second ingredient being ingredients of the same stock contained in a sample fluid, and also a third ingredient defined as the sum total of said first and second ingredients, said measurement being according to a differential method in which a third concentration of said third ingredient and a first concentration of said first ingredient are directly measured by means of detectors of the same kind and a second concentration of said second ingredient is indirectly measured from a difference between said third and first concentrations, comprising:
    two passage means for dividing said sample fluid into a first sample fluid and a second sample fluid flowing through the two passages, the passage of said first sample fluid being provided with a converter for one of removing the second ingredient from the first sample fluid, and converting the second ingredient to the first ingredient therein to serve as one of a line for use in the measurement of the first concentration of the first ingredient and a line for use in the measurement of the concentration of the third ingredient, the passage of said second sample fluid being provided without a converter to serve as one of a line for use in the measurement of the concentration of the third ingredient (total concentration) and a line for use in the measurement of the first concentration of the first ingredient;
    fluid modulation means for subjecting said converted first sample fluid and said unconverted second sample fluid to a fluid modulation by a reference fluid at two frequencies different from each other, said fluid modulation means being provided in both passages;
    an analyzer provided with only one detector capable of detecting both the concentration of said first ingredient and the concentration of said third ingredient and providing an output signal; and
    means for processing the output signal from said detector to divide it into signal components respectively having one of the two modulation frequencies of said first and second sample fluids followed by rectifying and levelling to separately measure said concentration of the first ingredient and said concentration of the third ingredient, whereby said concentration of the second ingredient is able to be measured from the difference between the results of the measurement of the first and third concentrations.

5. A gas analyzer, comprising:
    two cells having different cell-lengths and disposed between a light source and a detector in series;
    two fluid modulation means for simultaneously and continuously supplying said respective cells with a sample gas and a reference gas at an appointed period in a changed-over manner, one of said fluid modulation means being provided for each respective cell, modulation frequencies of the sample gas and the reference gas by the two modulation means being adapted to be different from each other; and
    means for measuring a concentration of an ingredient to be measured in the sample gas to enable the ingredient to be measured over a lower concentration to a higher concentration range by dividing an output from said detector into signal components respectively having the modulation frequencies of said sample gas and said reference gas for said respective cells which is followed by rectifying and levelling the signal components.

6. A gas analyzer, comprising:

two cells being disposed in parallel to each other and between a light source and a detector;

a filter having an absorption band at a wavelength which is almost the same as a characteristic absorption wavelength of an ingredient to be measured, said filter being disposed in an optical path on a side of one cell;

two fluid modulation means for simultaneously and continuously supplying said respective cells with a sample gas and a reference gas at an appointed period in a changed-over manner, one of said fluid modulation means being provided for each respective cell, modulation frequencies of the sample gas and the reference gas by the two modulation means being adapted to be different from each other; and means for measuring a concentration of an ingredient to be measured in the sample gas by dividing an output signal from said detector into separate signal components respectively having the modulation frequencies of said sample gas and said reference gas for said respective cells which is followed by rectifying, levelling and taking a difference between the signal components.

7. A two-ingredient measurement-type gas analyzer, comprising:

two cells being disposed in parallel between a light source and a detector;

a filter, having an absorption band at a wavelength which is almost the same as a characteristic absorption wavelength of an ingredient to be measured, being provided for each respective cell;

a pair of fluid modulation means for simultaneously and continuously supplying said respective cells with a sample gas and a reference gas at an appointed period in a changed-over manner for said respective cells, modulation frequencies of the sample gas and the reference gas by these two modulation means being adapted to be different from each other; and means for processing an output signal from said detector so as to divide the output signal into signal components respectively having the modulation frequencies of said sample gas and said reference gas for said respective cells which is followed by rectifying and levelling the signal components to obtain a measurement of each respective ingredient.

8. Apparatus for analyzing components of sample fluids, divided into a plurality of sample portions, comprising:

sensor means for providing an output signal indicative of a component to be measured in a sample fluid;

means for modulating sample portions to provide at least two different modulation frequencies at the same time, each frequency being characteristic of a specific sample portion delivered to the sensor means;

means for mixing the sample portions and simultaneously supplying the mixed sample portions to the sensor means; and means for processing the output signal relative to the modulation frequencies to correlate a portion of the output signal with the appropriate modulated sample portions to enable a determination of the component within each sample portion.

9. The apparatus of claim 8 further including means for modulating a sample fluid with the highest concentration of the characteristic to be sensed with a modulation frequency lower than another sample fluid with a lower concentration of the characteristic.

10. The apparatus of claim 8 further including means for adjusting a flow rate of a sample fluid with the highest concentration of the characteristic to be sensed to a lower flow rate than another sample fluid with a lower concentration of the characteristic.

* * * * *